United States Patent [19]
Aebi et al.

[11] Patent Number: 5,856,503
[45] Date of Patent: Jan. 5, 1999

[54] AMINOALKYL-SUBSTITUTED BENZO-HETEROCYCLIC COMPOUNDS

[75] Inventors: Johannes Aebi, Basel, Switzerland; Henrietta Dehmlow, Grenzach-Wyhlen, Germany; Jacques Himber, Guebwiller, France; Hans-Peter Märki; Hans Lengsfeld, both of Basel, Switzerland; Olivier Morand, Hegenheim, France; Gérard Schmid, Kienberg; Yu-Hua Ji, Basel, both of Switzerland

[73] Assignee: Hoffmann-La Roche Inc., Nutley, N.J.

[21] Appl. No.: 762,867

[22] Filed: Dec. 6, 1996

[30] Foreign Application Priority Data

Dec. 8, 1995 [CH] Switzerland ............... 3480/95

[51] Int. Cl.$^6$ ............ C07D 261/20; C07D 275/04; A61K 31/38; A61K 31/40

[52] U.S. Cl. ............ 548/207; 514/403; 514/248; 514/307; 514/311; 514/379; 514/372; 514/443; 514/469; 544/235; 544/49; 544/63; 546/152; 546/165; 546/149; 546/150; 548/241; 549/32; 549/462; 549/469

[58] Field of Search ............ 548/207

[56] References Cited

U.S. PATENT DOCUMENTS 4,956,371 9/1990 Shoupe et al. ............ 514/307

FOREIGN PATENT DOCUMENTS 636 367 1/1995 European Pat. Off. .
206 872 7/1994 Japan .

OTHER PUBLICATIONS

Abstract 122:187576 for Document B1.
Gamble et al., J. Lipi Res., 19, pp. 1068–1071 (1978).
Gotto et al., Circulation, *81*:172101733 (1990).
Hennes et al., Science Tools, 36, pp. 10–12 (1992).
Stein et al., Nutr. Metab. Cardiovasc. Dis., 2:113–156 (1992).
Abstract for Document B2.

*Primary Examiner*—Matthew V. Grumbling
*Attorney, Agent, or Firm*—George W. Johnston; William H. Epstein; John P. Parise

[57] ABSTRACT

Aminoalkyl-substituted benzo-heterocyclic compounds of the formula

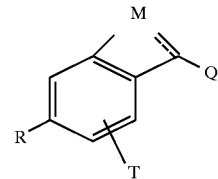

wherein M, Q, R and T are as defined in the specification, as well as acid addition salts thereof. These compounds are useful as cholesterol level lowering agents and as antimycotic agents.

30 Claims, No Drawings

AMINOALKYL-SUBSTITUTED BENZO-HETEROCYCLIC COMPOUNDS

BACKGROUND OF THE INVENTION

1. Field

The present invention is concerned with novel aminoalkyl-substituted benzo-heterocyclic compounds, a process for their manufacture, pharmaceutical preparations which contain such compounds, and the use of these compounds in the production of pharmaceutical preparations.

2. Description

There has been a long felt need for compounds which have cholesterol level lowering and antimycotic activity. The subject invention addresses this need.

SUMMARY OF THE INVENTION

The subject invention provides compounds of the formula:

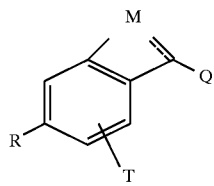

wherein

R is either a group of the formula:

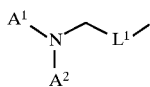

T is H, $C_1$–$C_6$ alkyl, halogen, $N(R^2,R^{21})$, $CONH_2$, CN, $NO_2$, $CF_3$, OH, $C_1$–$C_6$ alkyl(O), or $C_1$–$C_6$ alkyl(S), $R^2$ and $R^{21}$ are independently $C_1$–$C_6$ alkyl or H, and Q is $C_3$–$C_6$ cycloalkyl, phenyl substituted by $R^3$, $C_2$–$C_6$ alkenyl, $C_2$–$C_6$ alkenyl substituted by OH, $C_4$–$C_6$ alkadienyl, or $C_4$–$C_6$ alkadienyl substituted by OH, or when M is not interrupted by an O atom, then Q can also be $C_1$–$C_6$ alkyl or $C_1$–$C_6$ alkyl substituted by OH, or wherein one of R and T is halogen or H, and the other of R and T is H, $C_1$–$C_6$ alkyl, halogen, $N(R^2,R^{21})$, $CONH_2$, CN, $NO_2$, $CF_3$, OH, $C_1$–$C_6$ alkyl(O), or $C_1$–$C_6$ alkyl(S), and Q is a group of the formula:

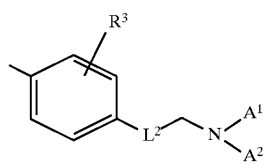

$A^1$ is $C_1$–$C_6$ alkyl or $C_3$–$C_6$ alkenyl, and $A^2$ is $C_3$–$C_6$ cycloalkyl, $C_3$–$C_6$ cycloalkyl-$C_1$–$C_6$-alkyl, $C_1$–$C_6$ alkyl, $C_1$–$C_6$ alkyl substituted by $R^4$, $C_2$–$C_6$ alkenyl, or $C_2$–$C_6$ alkenyl substituted by $R^4$, or $A^1$ and $A^2$ together are a $C_2$–$C_5$ alkylene, a $C_2$–$C_5$ alkylene substituted by $R^4$, $C_4$–$C_5$ alkenylene, or a $C_4$–$C_5$ alkenylene substituted by $R^4$ group $A^1$–$A^2$, $R^4$ is OH, $C_1$–$C_6$ alkyl(O) or $C_1$–$C_6$ alkyl(S) bonded to a saturated C atom of $A^2$ or of $A^1$–$A^2$, whereby a C atom substituted by $R^4$ or an unsaturated C atom present in $A^1$, $A^2$ or $A^1$–$A^2$ is bonded in a position other than the α-position to $N(A^1A^2)$, $L^1$ is a group L bonded to the benzo group directly or via O, NH, $N(C_1$–$C_6$ alkyl), or $N(C_1$–$C_6$ alkanoyl), $L^2$ is a group L bonded to the phenyl group via O, NH, $N(C_1$–$C_6$ alkyl), or $N(C_1$–$C_6$ alkanoyl), L is a $C_4$–$C_{11}$ alkylene, $C_3$–$C_{11}$ alkenylene, or ($C_{3-6}$-cyclo-alkylene)-($C_{1-C13}$ alkylene) bonded to the methylene group via its cycloalkylene group, $R^3$ is independently H, $C_1$–$C_6$ alkyl, halogen, $N(R^5, R^{51})$, $CONH_2$, CN, $NO_2$, $CF_3$, OH, $C_1$–$C_6$ alkyl(O), or $C_1$–$C_6$ alkyl(S), $R^5$ and $R^{51}$ are $C_1$–$C_6$ alkyl or H;

---- is a single bond or a double bond:

M is either (i) a two-membered grouping having 0 or 1 member selected from the group consisting of O, S, SO, $SO_2$ and CO; O, 1 or 2 members selected from the group consisting of N and $N(R^6)$; and O, 1 or 2 members selected from the group consisting of $C(R^6)$ and $CH(R^6)$, provided that at least one hetero atom or substituted hetero atom is in the grouping, or (ii) a three-membered grouping having 0 or 1 member selected from the group consisting of O, S, SO, $SO_2$ and CO; O; 1 or 2 members selected from the group consisting of N and $N(R^6)$; and O, 1 or 2 members selected from the group consisting of $C(R^6)$ and $CH(R^6)$, provided at least one hetero atom or substituted hetero atom is in the grouping; and $R^6$ is H or $C_1$–$C_6$ alkyl;

and physiologically useful acid addition salts thereof.

Also provided are compounds of the formula:

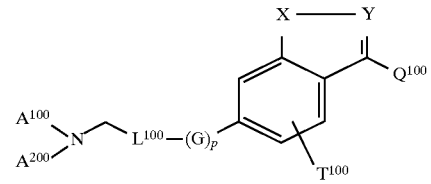

wherein $A^{100}$ is $C_1$–$C_6$ alkyl or $C_3$–$C_6$ alkenyl;

$A^{200}$ is $C_3$–$C_6$ cycloalkyl, $C_3$–$C_6$ cycloalkyl-$C_1$–$C_6$-alkyl, $C_1$–$C_6$ alkyl, $C_1$–$C_6$ alkyl substituted with OH or $O(C_1$–$C_6$ alkyl), $C_3$–$C_6$alkenyl, $C_3$–$C_6$ alkenyl substituted with OH or $O(C_1$–$C_6$ alkyl), or $CH_2CH_2SCH_3$;

$L^{100}$ is $C_4$–$C_{11}$ alkylene, $C_3$–$C_{11}$ alkenylene, or ($C_3$–$C_6$ cycloalkylene)-($C_1$–$C_{13}$ alkylene) bonded to the methylene group via its cycloalkyl group;

P is O or 1;

G is O, NH, $N(C_1$–$C_6$ alkyl) or $N(C_1$–$C_6$ alkanoyl);

$T^{100}$ is H, $C_1$–$C_6$ alkyl, halogen, $NH_2$, $NH(C_1$–$C_6$ alkyl), $N(C_1$–$C_6$ alkyl)$_2$, $CONH_2$, CN, $NO_2$, $CF_3$, OH, $C_1$–$C_6$ alkyl-O, or $C_1$–$C_6$ alkyl-S;

x is O, S, $SO_2$, NH or $N(C_1$–$C_6$ alkyl);

Y is N or CH; and $Q^{100}$ is $C_3$–$C_6$ cycloalkyl, $C_2$–$C_6$ alkenyl, $C_2$–$C_6$ alkenyl substituted with OH, $C_4$–$C_6$ alkadienyl, $C_4$–$C_6$ alkadienyl substituted with OH, or phenyl substituted with at least one substituent selected from the group consisting of H, $C_1$–$C_6$ alkyl, halogen, $NH_2$, $NH(C_1$–$C_6$ alkyl, $N(C_1$–$C_6$ alkyl)$_2$, $CONH_2$, CN, $NO_2$, $CF_3$, OH, $C_1$–$C_6$ alkyl-O and $C_1$–$C_6$ alkyl-S, or when X is not oxygen, then $Q^{100}$ can be $C_1$–$C_6$ alkyl or $C_1$–$C_6$ alkyl substituted with OH; and physiologically useful acid addition salts thereof.

Preferred versions of the above compounds are wherein $A^{100}$ is $C_1$–$C_6$ alkyl or $C_3$–$C_6$ alkenyl;

$A^{200}$ is $C_3$–$C_6$ cycloalkyl, $C_3$–$C_6$ cycloalkyl-$C_1$–$C_6$-alkyl, $C_1$–$C_6$ alkyl, or $C_3$–$C_6$ alkenyl;

$L^{100}$ is $C_4$–$C_6$ alkylene, $C_3$–$C_6$ alkenylene, or ($C_3$–$C_6$ cycloalkylene)-($C_1$–$C_6$ alkylene) bonded to the methylene group via its cycloalkyl group;

P is 1

G is O, NH, N($C_1$–$C_3$ alkyl) or N($C_1$–$C_3$ alkanoyl);

$T^{100}$ is H, $C_1$–$C_3$ alkyl, halogen, $NH_2$, CN, $NO_2$, $CF_3$ or OH;

X is O, S, $SO_2$, NH or N($C_1$–$C_3$ alkyl);

Y is N or CH; and $Q^{100}$ is $C_2$–$C_6$ alkenyl, $C_2$–$C_6$ alkenyl substituted with OH, $C_4$–$C_6$ alkadienyl, $C_4$–$C_6$ alkadienyl substituted with OH, or phenyl substituted with a substituent selected from the group consisting of H, halogen, $NH_2$, $CONH_2$, CN, $NO_2$, $CF_3$, $C_1$–$C_6$ alkyl-O and $C_1$–$C_6$ alkyl-S.

Even more preferred versions of the above compounds are wherein $A^{100}$ is methyl;

$A^{200}$ is allyl, cyclopropyl or methylsulphanyl-ethyl;

$L^{100}$ is $C_4$–$C_6$ alkylene or $C_3$–$C_6$ alkenylene;

P is 1;

G is O;

$T^{100}$ is H or F;

X is O, S, $SO_2$, NH or $NCH_3$;

Y is N or CH; and $Q^{100}$ is $C_2$–$C_6$ alkenyl or phenyl substituted with bromine.

Preferred compounds include allyl-[6-[3-(4-bromo-phenyl)-benzo[d]isothiazol-6-yloxy]-hexyl]-methyl-amine, 6-[3-(4-bromo-phenyl)-benzo[d]isothiazol-6-yloxy]-hexyl]-methyl-(2-methylsulphanyl-ethyl)-amine, allyl-[6-[3-(4-bromo-phenyl)-benzo[b]thiophen-6-yloxy]-hexyl]-methyl-amine, (E)-allyl-methyl-[4-[3-(4-methyl-pent-3-enyl)-benzo[d]isothiazol-6-yloxy]-but-2-enyl]-amine, is (E)-allyl-[4-[3-(4-bromo-phenyl)-benzo[d]isoxazol6-yloxy]-but-2-enyl-methyl-amine, (E)-allyl-[4-[3-(4-bromo-phenyl)-5-fluoro-1-methyl-1H-indazol-6-yloxy]-but-2-enyl]-methyl-amine, allyl-methyl-[6-[1-methyl-3-(4-methyl-pent-3-enyl)-1H-indazol-6-yloxy]-hexyl]-amine, (E)-allyl-methyl-[4-[1-methyl-3-(4-methyl-pent-3-enyl)-1H-indazol-6-yloxy]-but-2-enyl]-amine, [6-[3-(4-bromo-phenyl)-1-methyl-1H-indazol-6-yloxy]-hexyl]-cyclopropyl-methyl-amine, and allyl-[6-[3-(4-bromo-phenyl)-1H-indazol-6-yloxy]-hexyl]-methyl-amine.

DETAILED DESCRIPTION OF THE INVENTION

The subject invention will be described in terms of its preferred embodiments. These embodiments are set forth to aid in understanding the invention, but are not limiting.

In particular, the invention is concerned with aminoalkyl-substituted benzo-heterocyclic compounds of the formula

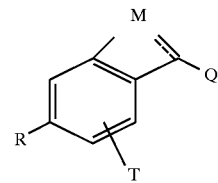

(I)

wherein

R is either a group of the formula

(R')

T is H, alkyl, halogen, $N(R^2,R^{21})$, $CONH_2$, CN, $NO_2$, $CF_3$, OH or alkyl(O or S), $R^2$ and $R^{21}$ are alkyl or H and Q is cycloalkyl, phenyl substituted by $R^3$ or an alkenyl or alkadienyl group with up to 13 C atoms optionally substituted by OH or, when M is not interrupted by an O atom, then Q can also be $C_1$–$C_{13}$-alkyl optionally substituted by OH, or wherein one of R and T is halogen or H and the other is H, alkyl, halogen, $N(R^2,R^{21})$, $CONH_2$, CN, $NO_2$, $CF_3$, OH or alkyl(O or S) and Q is a group of the formula

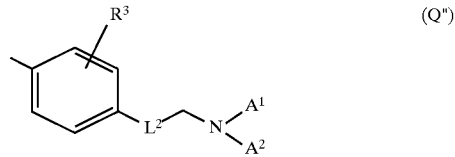

(Q")

$A^1$ is alkyl or alkenyl and $A^2$ is cycloalkyl, cycloalkyl-alkyl or an alkyl or alkenyl group optionally substituted by $R^4$ or $A^1$ and $A^2$ together are an alkylene or alkenylene group $A^1$–$A^2$ with up to 5 C atoms optionally substituted by $R^4$, $R^4$ is OH or alkyl(O or S) bonded to a saturated C atom of $A^2$ or of $A^1$–$A^2$, whereby a C atom substituted by $R^4$ or an unsaturated C atom present in $A^1$, $A^2$ or $A^1$–$A^2$ should be bonded in a position other than the α-position to $N(A^1A^2)$, $L^1$ is a group L bonded to the benzo group directly or via O, NH or N(alkyl or alkanoyl), $L^2$ is a group L bonded to the phenyl group via O, NH or N(alkyl or alkanoyl), L is an alkylene or alkenylene group with in total up to 11 C atoms and at least 4 or, respectively, 3 C atoms between the two free valencies or a ($C_{3-6}$-cycloalkylene)-alkylene group bonded to the methylene group via the cycloalkylene group, $R^3$ and $R^{31}$ are H, alkyl, halogen, $N(R^5,R^{51})$, $CONH_2$, CN, $NO_2$, $CF_3$, OH or alkyl(O or S), $R^5$ and $R^{51}$ are alkyl or H, the dotted bond emanating from M is optional, M is a 2- or 3-membered grouping which can contain an O or S atom or a group S(O), $S(O)_2$ or C(O) and/or up to two N atoms or groups $N(R^6)$ and/or up to two groups $C(R^6)$ or $CH(R^6)$, but which in total contains at least one optionally substituted hetero atom and $R^6$ is H or alkyl, and acid addition salts thereof.

In the scope of the present invention terms such as "alkyl", "alkenyl" and "alkadienyl" alone or in combination as in cycloalkyl-alkyl denote monovalent and, unless indicated otherwise, straight-chain or branched groups with up to 20, especially up to 13, preferably up to 8, C atoms, in the case of alkyl and alkenyl up to 6, especially up to 4, C atoms. Examples of alkyl are methyl, ethyl, propyl, isopropyl, n-, s- and t-butyl, pentyl, hexyl, decyl and dodecyl, of alkanoyl: formyl and acetyl, of alkenyl: vinyl, allyl, propenyl, butenyl, 3-methyl-2-butenyl, 4-methyl-3-pentenyl and undodecenyl, of alkadienyl: 4-methyl-1,3-pentadienyl; 3,7-dimethyl-2,6-octadienyl and 4,8-dimethyl-3,7-nonadienyl. "Alkylene" and "alkenylene" denote the divalent groups corresponding to the monovalent alkyl and, respectively, alkenyl groups defined above, such as pentylene and 3-methyl-pentylene; propenylene and 2,6-dimethyl-1-hexenylene. "Cycloalkyl" and "cycloalkylene" alone or in combination contain 3 to 6 C atoms such as cyclopropyl and cyclohexyl and, respectively, cyclopropylene.

Preferably, $A^1$ stands for methyl or allyl; $A^2$ stands for methyl, allyl, 2-methylsulphanyl-ethyl or cyclopropyl; $L^1$ and $L^2$ stand for $(CH_2)_5O$, $CH=CHCH_2O$ or cyclopropylene-methyleneoxy; Q stands for bromophenyl, methyl, 4-methyl-3-pentenyl, 2-hydroxy-4-methyl-3-pentenyl or 4-methyl-2,4-pentadienyl; R and T stand for H or F; $R^3$ stands for H, Br or F and $R^6$ stands for H or methyl.

Salts of the compounds I with inorganic and organic acids such as HCl, HBr, $H_2SO_4$, $HNO_3$, citric acid, acetic acid, succinic acid, fumaric acid, tartaric acid, methanesulphonic acid and p-toluenesulphonic acid come into consideration as pharmaceutically acceptable acid addition salts.

The compounds of formula I, which contain one or more asymmetric C atoms, can be present as enantiomers, as diastereomers or as mixtures thereof, such as racemates.

Compounds falling under formula I are:

a) those of the formula

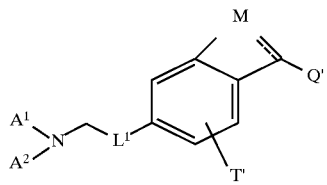

wherein

T is H, alkyl, halogen, $N(R^2,R^21)$, $CONH_2$, CN, $NO_2$, $CF_3$, OH or alkyl(O or S), Q' is cycloalkyl, phenyl substituted by $R^3$ or an alkenyl or alkadienyl group with up to 13 C atoms optionally substituted by OH or, when M is not interrupted by an O atom, then Q can also be $C_{1-13}$-alkyl optionally substituted by OH, $L^1$ is a group L bonded to the benzo group directly or via O, NH or N(alkyl or alkanoyl) and $A^1, A^2, L, M, R^2, R^{21}$ and $R^3$ have the above significance, b) those of the formula

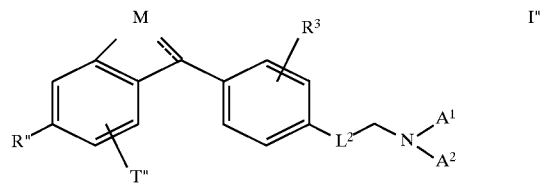

wherein one of R" and T" is halogen or H and the other is H, alkyl, halogen, $N(R^2,R^{21})$, $CONH_2$, CN, $NO_2$, $CF_3$, OH or alkyl(O or S), $L^2$ is a group L bonded to the phenyl group via O, NH or N(alkyl or alkanoyl) and $A^1, A^2, L, M, R^2, R^{21}$ and $R^3$ have the above significance.

Preferred among the compounds in accordance with the invention are:

A) those of the formula

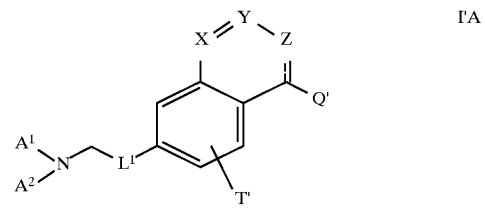

wherein the grouping X=Y—Z contains one or two N-atoms and two or, respectively, one CH or C(alkyl) group, especially in which X=Y—Z is a grouping CH=CH—N, CH=N—N, N=CH—N, N=CH—NH, N=CH—CH or N=C(alkyl)—CH, particularly N=C(CH$_3$)—CH, B) those of the formula

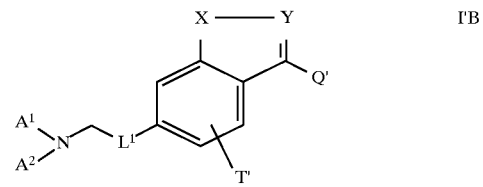

wherein X is an O or S atom or a $SO_2$, NH or N(alkyl) group, especially N(CH$_3$), and Y is a N atom or CH, C) those of the formula

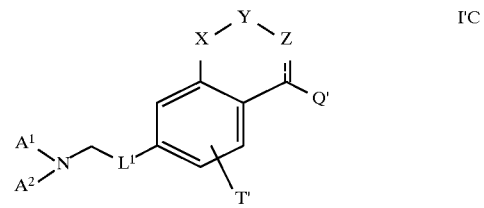

wherein the grouping X—Y—Z can contain an O atom or a group C(O) and/or up to two N atoms or N(R$^6$) groups and/or up to two C(R$^6$) or CH(R$^6$) groups, but contains in total one or two optionally substituted hetero atoms, especially in which X—Y—Z is a grouping CH$_2$—O—N, O—CH$_2$—CH, CH$_2$—CH$_2$—N, N(R$^6$)—C(O)—N, especially N(CH$_3$)—C(O)—N or CH$_2$—CH$_2$—N(R$^6$), particularly CH$_2$—CH$_2$—NH or CH$_2$—CH$_2$—N(CH$_3$), D) those of the formula

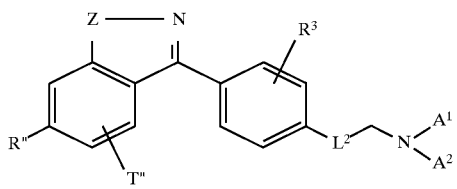

wherein Z is an O or S atom or a $SO_2$ or N(alkyl) group, especially N—methyl, or wherein Z and N together are the $CH_2$—O—N group.

Preferred compounds of formula I'A are those in which $A^1$ is alkyl, $A^2$ is alkenyl or cycloalkyl, T' is hydrogen, Q' is phenyl substituted by $R^3$ and $L^1$ is a group L bonded to the benzo group via an O atom and/or in which X=Y—Z is a grouping CH=CH—N, CH=N—N, N=CH—N or N=CH—CH, especially in which $A^1$ is methyl, $A^2$ is allyl or cyclopropyl, $L^1$ is n-pentyleneoxy or cyclopropylenemethyleneoxy, T' is hydrogen and Q' is phenyl substituted by bromine, particularly the compounds:

Allyl-[6-[1-(4-bromo-phenyl)-isoquinolin-6-yloxy]-hexyl]-methyl-amine (E)-allyl-[4-[1-(4-bromo-phenyl)-isoquinolin-6-yloxy]-but-2-enyl]-methyl-amine allyl-[6-[1-(4-bromo-phenyl)-phthalazin-6-yloxy]-hexyl]-methyl-amine allyl-[6-[4-(4-bromo-phenyl)-quinazolin-7-yloxy]-hexyl]-methyl-amine allyl-[6-[4-(4-bromo-phenyl)-quinolin-7-yloxyl-hexyl]-methyl-amine and (1RS,2RS)-[2-[1-(4-bromo-phenyl)-isoquinolin-6-yloxymethyl]-cyclopropylmethyl]-cyclopropyl-methyl-amine as well as the compounds:

(E)-Allyl-[4-[1-(4-bromo-phenyl)-isoquinolin-6-yloxy]-but-2-enyl]-methyl-amine

5-[4-(allyl-methyl-amino)-but-2-enyloxy]-2-(4-bromo-benzoyl)-benzaldehyde and allyl-[6-[4-(4-bromo-phenyl)-2-methyl-quinolin-7-yloxy]hexyl]-methyl-amine.

Preferred compounds of formula I'B are those in which $A^1$ is alkyl, $A^2$ is alkenyl, cycloalkyl or alkyl-S-alkyl, $L^1$ is an alkylene or alkenylene group with a total of up to 11 C atoms and at least 4 or, respectively, 3 C atoms between the two free valencies bonded to the benzo group via an O atom, T' is hydrogen or halogen and T' is phenyl substituted by $R^3$ or an alkyl or optionally OH-substituted alkenyl or alkadienyl group with up to 13 C atoms and/or in which X—Y is a S—CH, O—N, S—N, NH—N or $N(CH_3)$—N group, especially in which $A^1$ is methyl, $A^2$ is allyl, cyclopropyl or methylsulphanylethyl, $L^1$ is n-pentyleneoxy or n-propenyleneoxy, $Q^1$ is bromophenyl or 4-methyl-pent-3-enyl and T' is hydrogen or fluorine, particularly the compounds:

Allyl-[6-[3-(4-bromo-phenyl)-benzo[d]isothiazol-6-yloxy]-hexyl]-methyl-amine

6-[3-(4-bromo-phenyl)-benzo[d]isothiazol-6-yloxy]-hexyl]methyl-(2-methylsulphanyl-ethyl)-amine allyl-[6-[3-(4-bromo-phenyl)-benzo[b]thiophen-6-yloxy]hexyl]-methyl-amine (E)-allyl-methyl-[4-[3-(4-methyl-pent-3-enyl)-benzo[d]isothiazol-6-yloxy]-but-2-enyl]-amine (E)-allyl-[4-[3-(4-bromo-phenyl)-benzo[d]isoxazol-6-yloxy]but-2-enyl-methyl-amine (E)-allyl-[4-[3-(4-bromo-phenyl)-5-fluoro-1methyl-1H-indazol-6-yloxy]-but-2-enyl]-methyl-amine allyl-methyl-[6-[1-methyl-3-(4-methyl-pent-3-enyl)-1H indazol-6-yloxy]-hexyl]-amine (E)-allyl-methyl-[4-[1-methyl-3-(4-methyl-pent-3-enyl)-1H-indazol-6-yloxy]-but-2-enyl]-amine

[6-[3-(4-bromo-phenyl)-1-methyl-1H-indazol-6-yloxy]hexyl]-cyclopropyl-methyl-amine and allyl-[6-[3-(4-bromo-phenyl)-1H-indazol-6-yloxy]-hexyl]methyl-amine as well as the compounds:

(E)-Allyl -[4-[3-(4-bromo-phenyl)-benzo[d]isothiazol-6-yloxy]but-2-enyl]-methyl-amine (E)-[4-[3-(4-bromo-phenyl)-benzo[d]isothiazol-6-yloxy]-but-2-enyl]-methyl-(2-methylsulphanyl-ethyl)-amine allyl-methyl-[6-(3-methyl -benzo[d]isothiazol-6-yloxy) hexyl]-amine (E)-allyl-methyl-[4-(3-methyl-benzo[d]isothiazol-6-yloxy) but-2-enyl]-amine (E)-allyl-[4-[3-(4-bromo-phenyl)-benzo[b]thiopen-6-yloxy]but-2-enyl]-methyl-amine allyl-methyl-[6-[3-(4-methyl-pent-3-enyl)-benzo[d]isothiazol-6-yloxy]-hexyl-amine (E)-allyl-methyl-[6-[3-(4-methyl-penta-1,3-dienyl)-benzo[d]isothiazol-6-yloxy]-hexyl]-amine (RS)-1-[6-[6-(allyl-methyl-amino)-hexyloxyl-benzo[d]isothiazol-3-yl]-4-methyl-pent-3-en-2-ol (E)-(RS)-1-[6-[4-(allyl-methyl-amino)-but-2-enyloxy] benzo[d]isothiazol-3-yl]-4-methyl-pent-3-en-2-ol allyl-methyl-[(E)-4-[3-[(E)-4-methyl-penta-1,3-dienyl] benzo[d]isothiazol-6-yloxy]-but-2-enyl]-amine 7:3 mixture of (E)-allyl-methyl-[6-[3-(4-methyl-penta-2, 4-dienyl)-benzo[d]isothiazol-6-yloxy]-hexyl]-amine and (E)-allyl-methyl-[6-[3-(4-methyl-penta-1,3-dienyl) -benzo[d]isothiazol-6-yloxy]-hexyl]-amine allyl-[6-[3-(4-bromo-1,1-dioxo-benzo[d]isothiazol-6-yloxy]hexyl]-methyl-amine allyl-[6-[3-(4-bromo-phenyl)-benzo[d]isoxazol-6-yloxy] hexyl]-methyl-amine

[6-[3-(4-bromo-phenyl)-benzo[d]isoxazol-6-yloxy]-hexyl]cyclopropyl-methyl-amine (E)-allyl-methyl-[4-[3-(4-methyl-pent-3-enyl)-benzo[d] isoxazol-6-yloxy]-but-2-enyl]-amine (E)-allyl-[4-[3-(4-bromo-phenyl)-benzofuran-6-yloxy]-but-2-enyl]-methyl-amine allyl-[6-[3-(4-bromo-phenyl)-benzofuran-6-yloxy]-hexyl]methyl-amine allyl-[6-[3-(4-bromo-phenyl)-1-methyl-1H-indazol-6-yloxy]hexyl]-methyl-amine (E)-allyl-[4-[3-(4-bromo-phenyl)-1-methyl-1H-indazol-6-yloxy]-but-2-enyl]-methyl-amine allyl-[6-(1,3-dimethyl-1H-indazol-6-yloxy)-hexyl]-methyl-amine (E)-allyl-[4-(1,3-dimethyl-1H-indazol-6-yloxy)-but-2-enyl]-methyl-amine and cyclopropyl-methyl-[6-[3-(4-methyl-pent-3-enyl)-1H indazol-6-yloxy]-hexyl]-amine.

Preferred compounds of formula I'C are those in which $A^1$ is alkyl, $A^2$ is alkenyl, $L^1$ is an alkylene or alkenylene group with a total of up to 11 C atoms and at least 4 or, respectively, 3 C atoms between the two free valencies bonded to the benzo group via an O atom, T' is hydrogen and Q' is phenyl substituted by $R^3$ and/or in which X—Y—Z is a $CH_2$—O—

N, $CH_2$—$CH_2$—N or O—$CH_2$—CH grouping, especially in which $A^1$ is methyl, $A^2$ is allyl, $L^1$ is n-pentyleneoxy or n-propenyleneoxy, T' is hydrogen and Q' is bromophenyl, particularly the compounds:

(E)-Allyl-[4-[1-(4-bromo-phenyl)-3,4-dihydro-isoquinolin-6-yloxy]-but-2-enyl]-methyl-amine (E)-allyl-[4-[4-(4-bromo-phenyl)-1H-benzo[d][1,2]oxazin-7-yloxy]-but-2-enyl]-methyl-amine and allyl-[6-[4-(4-bromo-phenyl)-2H-chromen-7-yloxy]-hexyl]methyl-amine as well as the compounds:

Allyl-[6-[1-(4-bromo-phenyl)-3,4-dihydro-isoquinolin-6-yloxy]-hexyl]-methyl-amine (RS)-allyl-[6-[1-(4-bromo-phenyl)-1,2,3,4-tetrahydro-isoquinolin-6-yloxy]-hexyl]-methyl-amine isoquinolin-6-yloxy]-hexyl]-methyl-amine (RS)-allyl-[6-[1-(4-bromo-phenyl)-2-methyl-1,2,3,4-tetrahydro-isoquinolin-6-yloxy]-hexyl]-methyl-amine allyl-6-[4-(4-bromo-phenyl)-1H-benzo[d][1,2]oxazin-7-yloxy]-hexyl-methyl-amine and 7-[6-(allyl-methyl-amino)-hexyloxy]-4-(4-bromo-phenyl)-1-methyl-1H-quinazolin-2-one.

Preferred compounds of formula I''d are those in which $A^1$ is alkyl, $A^2$ is alkenyl, $L^2$ is an alkylene or alkenylene group with a total of up to 11 C atoms and at least 4 or, respectively, 3 C atoms between the free valencies bonded to the phenyl group via an O atom, $R^3$ is hydrogen and R'' and T'' are hydrogen or halogen; and/or in which Z is an O or S atom or a $SO_2$ or N-methyl group or in which Z and N together are the $CH_2$—O—N group, especially in which $A^1$ is methyl, $A^2$ is allyl, $L^2$ is n-pentyleneoxy or n-propyleneoxy, $R^3$ is hydrogen or fluorine, R'' is hydrogen or bromine and T'' is hydrogen or fluorine, particularly the compounds:

Allyl-[6-[4-(6-bromo-benzo[d]isothiazol-3-yl)-phenoxy]hexyl]-methyl-amine (E)-allyl-[4-[4-(6-bromo-benzo[d]isothiazol-3-yl)-phenoxy]but-2-enyl]-methyl-amine allyl-[6-[4-(6-bromo-1,1-dioxo-benzo[d]isothiazol-3-yl)-phenoxy]-hexyl]-methyl-amine allyl-[6-[4-(6-bromo-benzo[d]isoxazol-3-yl)-phenoxy]-hexyl]-methyl-amine (E)-allyl-[4-[4-(6-bromo-benzo[d]isoxazol-3-yl)-phenoxy]but-2-enyl]-methyl-amine allyl-[6-[4-(7-bromo-1H-benzo[d][1,2]oxazin-4-yl)-phenoxy]hexyl]-methyl-amine (E)-allyl-[4-[4-(7-bromo-1H-benzo[d][1,2]oxazin-4-yl)phenoxy]-but-2-enyl-methyl-amine (E)-allyl-[4-[2-fluoro-4-(4-fluoro-1-methyl-1H-indazol-3-yl)-phenoxy]-but-2-enyl]-methyl-amine and allyl-[6-[4-(6-bromo-1-methyl-1H-indazol-3-yl)-phenoxy)hexyl]-methyl-amine.

The invention is also concerned with a process for the manufacture of the compounds of formula I. This process comprises a) reacting a bromide of the formula

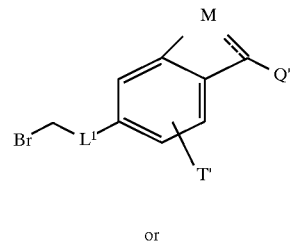

II' or

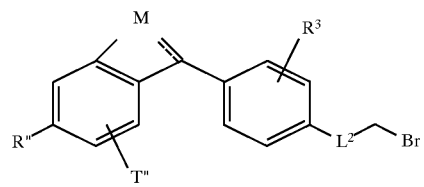

II'' with an amine $HN(A^1,A^2)$, b) cyclizing a ketone of the formula

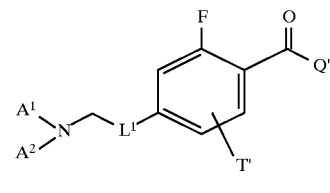

III' or

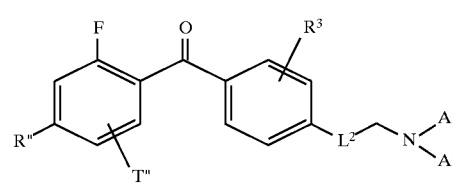

III'' by means of $H_2NNH-R^6$, c) cyclizing an oxime of the formula

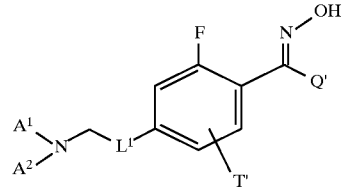

IV' or

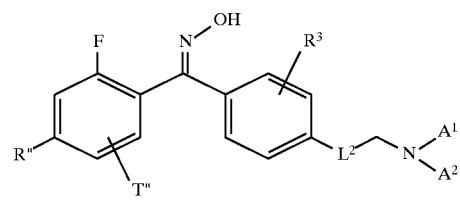

IV'' d) cyclizing an aldehyde of the formula

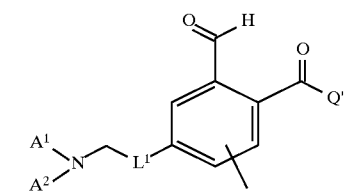

or

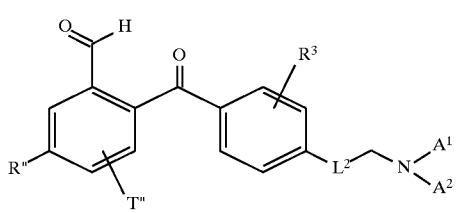

by means of hydrazine, e) cyclizing an amine of the formula

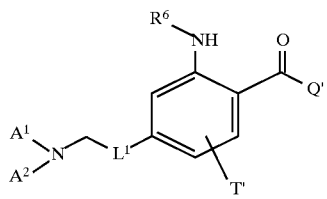

or

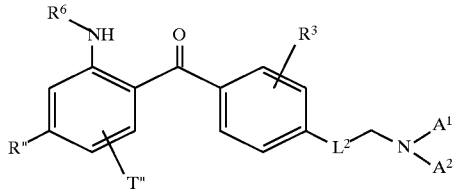

f) cyclizing a phenol of the formula

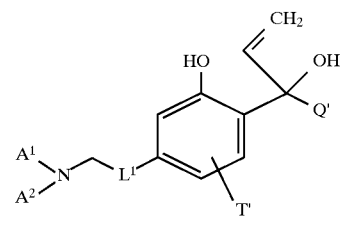

or

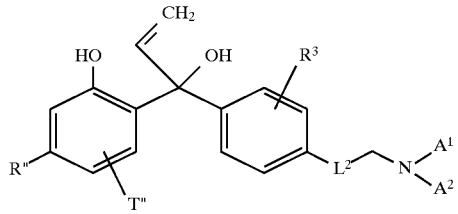

or an aniline of the formula

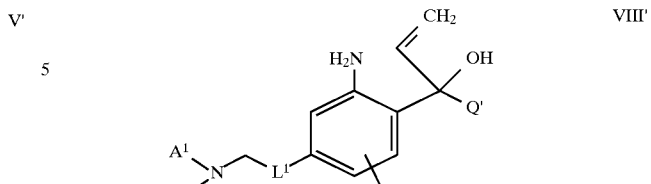

or

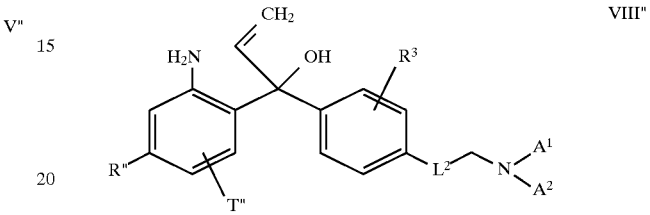

g) reacting a phenol of the formula

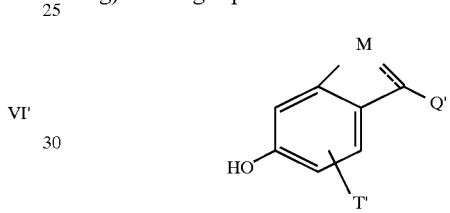

or

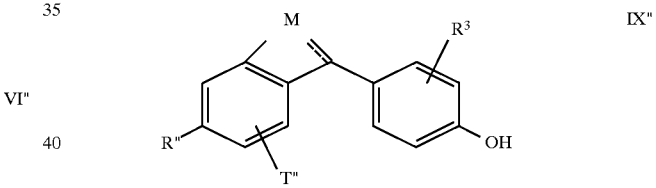

with an aminoalcohol $(A^1, A^2)NCH_2$—L—OH, h) if desired, functionally modifying a reactive group present in a compound of formula I and i) if desired, converting an amine of formula I into a physiologically compatible acid addition salt or converting an acid addition salt of a compound of formula I into the amine of formula I.

This process and those for the preparation of the starting materials of formulae II' and II" to IX' and IX" can be carried out in a manner known per se. Thus, the reaction a) of the bromide II' or II" with the amine $HN(A^1, A^2)$ is carried out in dimethylacetamide (DMA) or dimethylformamide (DMF) or in acetone in the presence of $K_2CO_3$.

Bromides II' (or II") in which $L^1$ (or $L^2$) is a group L bonded via O are obtained by reacting a dibromide $BrCH_2$—L—Br with a corresponding phenol of formula IX' or IX". Such a phenol is prepared from the corresponding methyl ether and the latter is prepared by cyclizing a methyl ether of the formula

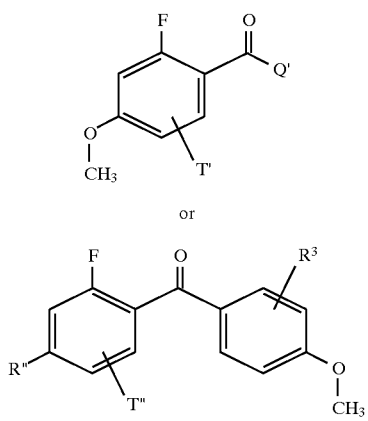 X' or

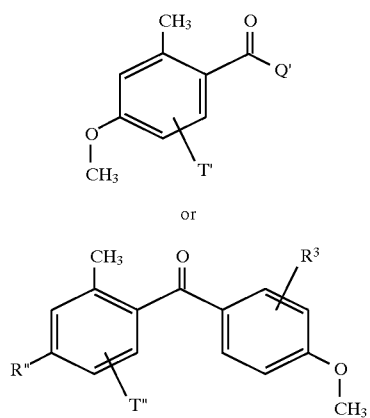 X"

This cyclization can be carried out by reacting the fluoride X' or X" using benzylmercaptan in the presence of potassium tert.butylate in THF, treating the benzylthio ether obtained with sulphuryl chloride in methylene chloride and cyclizing the resulting compound in THF with a solution of ammonia in ethanol.

In a variant, a methyl ether of the formula

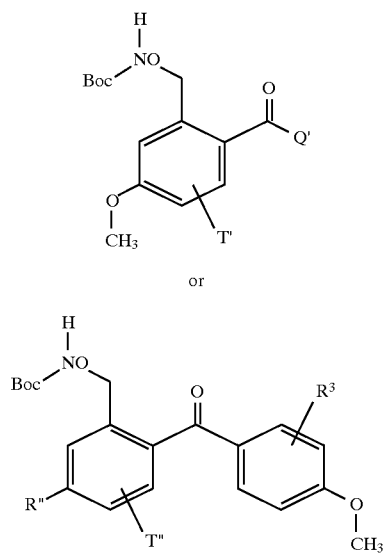

XI' or

XI"

is converted via a compound of the formula

XII' or

XII"

into the phenol of the formula

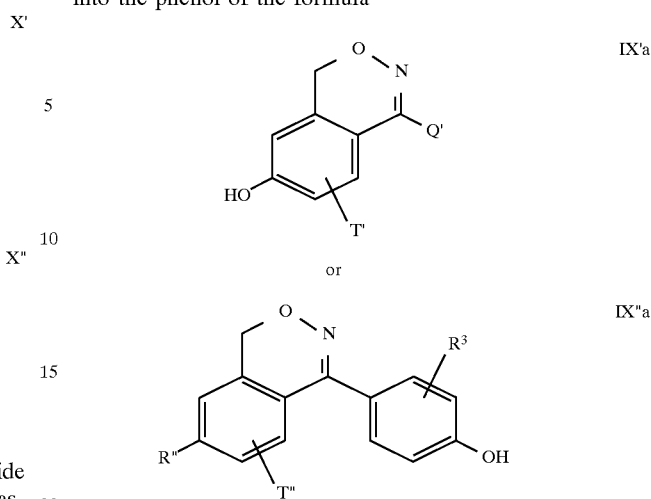 IX'a or

IX"a

The cyclization b) of a ketone III' or III" by means of an optionally alkylated hydrazine of the formula $H_2NNH-R^6$ is carried out in DMA in the presence of potassium carbonate at a temperature up to 150° C., preferably about 120° C. It leads to compounds of formula I in which M is a $N(R^6)$—N group.

Ketones III' and III" are obtained starting from the corresponding methyl ethers X' and, respectively, X" via the corresponding phenols, e.g. as described in Examples A and B hereinafter.

The cyclization c) of an oxime IV' or IV" is effected in DMA in the presence of potassium carbonate while heating at a temperature up to 160° C., preferably about 130° C. It leads to compounds I in which M is the ON group.

Oximes IV' and IV" are obtained by reacting the ketones III' and, respectively, III" with $NH_2OH, HCl$ in the presence of sodium acetate in ethanol while heating at a temperature of about 90° C.

An aldehyde V' or V" can be cyclized by means of hydrazine hydrate in ethanol to a compound of formula I in which M is the CH=N—N group. Aldehydes V' and V" are obtained starting from corresponding compounds of formulae XI' and, respectively, X" via the dibromides of the formulas

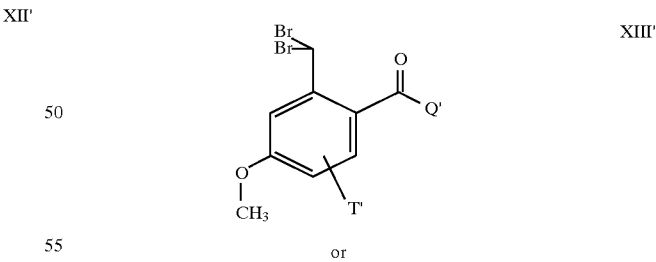 XIII' or

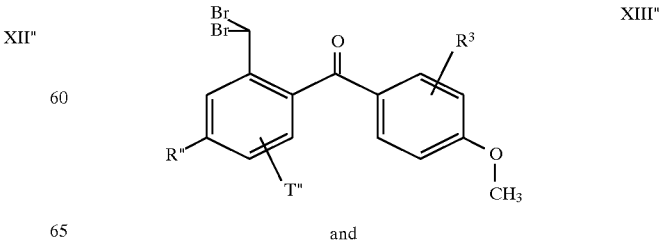 XIII"

and

-continued

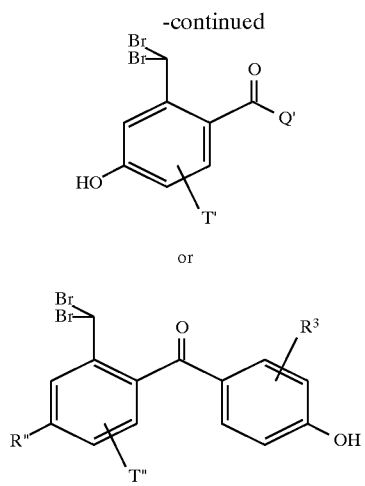

and the aldehydes of the formulas

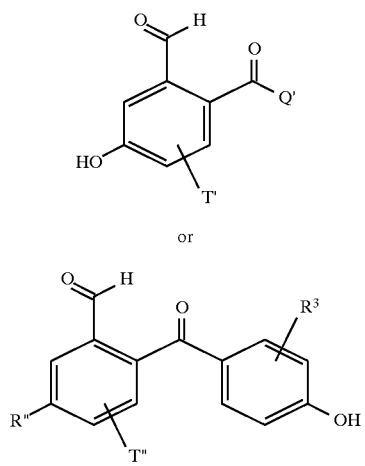

The cyclization e) of an amine of formula VI' or VI" leads to compounds of formula I in which M stands for N=CH—NH, N(R⁶)—C(O)—N or N=C(R⁶)—CH depending on whether 1) an amine VI' or VI" in which R⁶ stands for H is reacted with formic acid and formamide at an elevated temperature, 2) an amine VI' or VI" in which R⁶ is alkyl is reacted with chlorosulphonyl isocyanate in methylene chloride while cooling or 3) an amine VI' or VI" in which R⁶ stands for H is reacted with a ketone R⁶—C(O)—CH₃ in acetic acid and sulphuric acid while heating.

The amines VI' and VI" are obtained starting from the compounds III' and, respectively, III". The fluorine atom present in the latter compounds is transformed either into a free amino group by reaction with methoxybenzylamine in the presence of a base such as potassium carbonate in toluene and then with trifluoroacetic acid or into an alkylamino group R⁶—NH by reaction in DMA with an alkylamine R⁶—NH₂ in ethanol.

The cyclization of a phenol VII' (or VII") or of an aniline VIII' (or VIII") leads to a compound I in which M is a O—CH—CH or, respectively, N=CH—CH group. A phenol VII' or VII" is cyclized in a solvent such as o-xylene at an elevated temperature, preferably at the boiling point of the reaction solution, on a water separator. The cyclization of the aniline VIII' or VIII" is effected in a solvent such as methylene chloride in the presence of pyridinium chlorochromate while cooling, preferably to about 0° C.

Phenols VII' and VII" are obtained by reacting the corresponding compounds of the formulas with vinylmagnesium chloride in THF/diethyl ether at about 0° C. Analogously, anilines VIII' and VIII" are obtained from the corresponding compounds of formulae VI' and VI" in which R⁶ stands for H. The phenols XVI' and XVI" are obtained starting from the corresponding fluorides III' and III" firstly be reaction with sodium methanolate and subsequent cleavage of the resulting methyl ether by means of acetic acid/hydrobromic acid.

Reaction g) is carried out in a solution of triphenylphosphine, phenol of formula IX' or IX" and aminoalcohol of the formula (A¹, A²)NCH₂—L—OH in THF by means of diethyl azodicarboxylate.

The following can be mentioned as functional transformations h) of a reactive group present in a compound of formula I:

1) By deprotonizing a compound of formula I' in which Q' is methyl, firstly with lithium diisopropylamide in THF at −78° C. and then reacting at this temperature with a bromide BrCH₂—R⁷ or aldehyde HC(O)—R⁷, wherein R⁷ is an alkyl, alkenyl or alkadienyl group with up to 12 C atoms, there is obtained the corresponding compound I' in which Q' stands for CH₂CH₂—R⁷ or CH₂CH(OH)—R⁷.

2) By hydrogenating a compound I in which M is a CH₂—CH₂—N group, e.g. with sodium borohydride, this group can be transformed into the CH₂—CH₂—NH group.

3) A compound I in which M is the CH₂—CH₂—NH group can be methylated by means of formaldehyde in the presence of NaH₂PO₃ in dioxan to the corresponding compound I in which M is the CH₂—CH₂—N(CH₃) group.

The preparation of some of the aforementioned starting materials and intermediates is described in Examples A and B hereinafter.

The invention is concerned with the compound of formula I and their salts for use as therapeutically active substances, antimycotically-active and cholesterol-lowering medicaments containing a compound of formula I or a salt thereof as the active ingredient, if desired together with a therapeutically inert carrier, as well as the use of the compounds of formula I and the salts thereof for the production of the aforementioned medicaments.

Cholesterol is a major component of atherosclerotic plaques. The connection between coronary heart disease (CHD) and high LDL cholesterol concentrations in plasma (LDL=low density lipoproteins) and the therapeutic advantage of lowering elevated LDL concentrations are today generally recognized (Gotto et al., Circulation, 81:1721–1733 (1990) and Stein et al., Nutr. Metab. Cardiovasc. Dis., 2:113–156 (1992). Atherosclerotic plaques can grow and lead to occlusion of blood vessels resulting in an ischaemia or an infarct. Studies with respect to primary prophylaxis have shown that a lowering of the LDL concentrations in plasma reduces the frequency of non-fatal incidences of CHD, while the overall morbidity remains unchanged. The lowering of the LDL cholesterol level in plasma of patients with clinically confirmed CHD (secondary intervention) reduces the CHD-mediated mortality and morbidity; the metaanalysis of of different studies shows that this decrease is proportional to the reduction of the LDL cholesterol.

The clinical advantage of cholesterol lowering is even greater for patients with confirmed CHD than for asymptomatic persons with hypercholesterolemia. For the majority of patients who had survived a myocardial infarct as well as for patients suffering from angina pectoris or another atherosclerotic disease treatment with a lipid lowering agent is advisable, in which case a LDL cholesterol concentration of 2.6 mmol/l should be striven for.

Preparations such as cholanic acid sequestrating preparations, fibrate, nicotinic acid, probucol as well as the statins (HMG-Co-A reductase inhibitors) such as lovastatin and simvastatin are used for usual standard therapies. A new cholesterol-lowering medicament would be of considerable benefit for CHD patients having a high LDL cholesterol level and in which the striven-for value of 2.5 to 3.0 mmol/l can not be achieved with statins.

Further, statins have undesired side effects. They inhibit cholesterol production in an early phase of the synthesis cascade, with the formation of non-sterolic isoprenoids also being inhibited. The latter are indispensible for cell functions. The regulation of the cell cycle, the modification of albumins and the transport of electrons in the carbon dioxide chain can therefore be influenced by statins.

For this reason a number of experiments have been undertaken to find plasma-cholesterol lowering medicaments which inhibit the cholesterol synthesis on the one hand after the farnesyl-pyrophosphate stage in order not to inhibit the formation of non-sterolic isoprenoids and on the other hand prior to lanosterol in order to avoid an accumulation of sterol intermediates. The compounds described in European Patent Application No. 636 367, which inhibit 2,3-oxidosqualene-lanosterol cyclase (OSC) and which lower the total cholesterol in plasma, belong to these substances.

The present compounds of formula I inhibit cholesterol synthesis and reduce the total cholesterol in plasma. They can therefore be used in the therapy and prophylaxis of hypercholesterolemia, hyperlipemia and arteriosclerosis. In contrast to known compounds, the present compounds are tolerated better and more active. Further, they can be used in the therapy of mycoses and hyperproliferative disorders. The following tests were carried out in order to verify the activity of the compounds of formula I and their salts.

Inhibition of human liver microsomal 2,3-oxidosqualene-lanosterol cyclase (OSC)

Liver microsomes from a healthy volunteer were prepared in sodium phosphate buffer (pH 7.4). The OSC activity was measured in the same buffer which also contained 1 mM EDTA and 1 mM dithiothreitol. The microsomes were diluted to 0.8 mg/ml protein in cold phosphate buffer. Dry [$^{14}$C]R,S-monooxidosqualene (MOS; 12.8 $\mu$Ci/mmol) was diluted to 20 nCi/$\mu$l with ethanol and mixed with phosphate buffer-1% BSA (Bovine Serum Albumin). A stock solution of 1 mM test substance in DMSO was diluted to the desired concentration with phosphate buffer-1% BSA. 40 $\mu$l of microsomes were mixed with 20 $\mu$l of the solution of the test substance and the reaction was subsequently started with 20 $\mu$l of the [$^{14}$C]R,S-MOS solution. The final conditions were: 0.4 mg/ml of microsomal proteins and 30 $\mu$l of [$^{14}$C]R,S-MOS in phosphate buffer, pH 7.4, containing 0.5% albumin, DMSO <0.1% and ethanol <2%, in a total volume of 80 $\mu$l.

After 1 hour at 37° C. the reaction was stopped by the addition of 0.6 ml of 10% KOH-methanol, 0.7 ml of water and 0.1 ml of hexane:ether (1:1, v/v) which contained 25 $\mu$g of non-radioactive MOS and 25 $\mu$g of lanosterol as the carrier. After shaking 1 ml of hexane:ether (1:1, v/v) was added to each test tube, these were again shaken and then centrifuged. The upper phase was transferred into a glass test tube, the lower phase was again extracted with hexane:ether and combined with the first extract. The entire extract was evaporated to dryness with nitrogen, the residue was suspended in 50 $\mu$l of hexane:ether and applied to a silica gel plate. Chromatographic separation was effected in hexane:ether (1:1, v/v) as the eluent. The Rf values for the MOS substrate and the lanosterol product were 0.91 and, respectively, 0.54. After drying radioactive MOS and lanosterol were observed on the silica gel plate. The ratio of MOS to lanosterol was determined from the radioactive bands in order to determine the OSC inhibition.

The test was carried out on the one hand with a constant test substance concentration of 100 nM and the percentage OSC inhibition against controls was calculated. In addition, the test was carried out with different test substance concentrations and subsequently the IC$_{50}$ value was calculated, i.e. the concentration required to reduce the conversion of MOS into lanosterol to 50% of the control value. The results are given in the following Table:

| Product of Example No. | 1 | 2a | 2b | 3 | 6 | 12 | 14 | 23 | 24 | 26 | 27 | 29 | 31 | 32e | 32h | 32i | 32k | 33 | 37 | 38 | 39 |
|---|---|---|---|---|---|---|---|---|---|---|---|---|---|---|---|---|---|---|---|---|---|
| Inhibition of OSC (%) | 96 | 92 | 32 | 99 | 62 | 61 | 30 | 99 | 98 | 95 | 96 | 85 | 79 | 75 | 54 | 55 | 62 | 94 | 84 | 77 | 83 |
| IC$_{50}$ (nM) | 3.3 | 1.65 | | 4.0 | | | | 1.6 | | 2.1 | 3.7 | 29 | | | | | | 12.3 | 11.4 | 24 | 3.6 |

Cholesterol lowering in fat-fed hamsters

Male golden hamsters kept individually were pre-treated for 7 days with a diet containing grated coconut (40 cal. % fat). The animals were then divided into groups each comprising 5 animals. During the treatment the animals were maintained on the same diet. Each test substance was firstly homogenized in 9 ml of water and subsequently mixed with the milled diet. The controls received only feed converted into a paste with water. The animals were treated for 10 days with a test substance dosage of 200 $\mu$mol (about 70–120 mg/kg/day). Blood samples (200 $\mu$l) were removed via the jugular vein under light anaesthesia on the last day of the pretreatment and one day after the last administration of test substance. The plasma cholesterol concentration was determined using a colorimetric enzyme method. The plasma lipoproteins were separated by exclusion chromatography (Hennes et al., Science Tools, 36, 1992, 10–12). The total cholesterol was determined in each fraction using a fluorometric enzyme method (Gamble et al., J. Lipid Res., 19, 1978, 1068–1071) in order to calculate the amount of cholesterol in the LDL and HDL fractions. The activity on plasma cholesterol and LDL and HDL cholesterol, expressed in percent of the control animals, for the products of Examples 8a and 12 is reproduced in the following Table:

| Example | 1 | 23 |
|---|---|---|
| Total cholesterol | −33% | −15% |
| LDL cholesterol | −36% | −23% |
| HDL cholesterol | −27% | −2% |

As already mentioned, the compounds of formula I and their pharmaceutically acceptable acid addition salts have, moreover, valuable antifungal properties. They are active against a large number of pathogenic fungi which cause topical and systemic infections, such as Candida albicans, Cryptococcus neoformans and Aspergillus fumigatus.

Antifungal activity in vitro

The compounds were tested for antifungal activity against Candida albicans, Cryptococcus neoformans and Aspergillus fumigatus using a microdilution method on microtitre plates (96 wells per plate). Yeast supplemented with 1% glucose and 0.25% di-potassium phosphate was used for the three fungal strains. The fungal cells were inoculated at $3 \times 10^4$ CFU (Colony Forming Unit) in 1 ml of medium per well. The medium contained increasing concentrations of test substance. After incubation at 27° C. for 24 or 48 hours the turbidity in each well was measured by a microtitre plate reader. The growth inhibition was calculated in comparison to (without test substance). The $IC_{50}$ value given in the following Table is the concentration of test substance at which the growth is inhibited by 50%.

| Compound of Example No. | $IC_{50}$ (mg/ml) for: | | | |
|---|---|---|---|---|
| | C. albicans after: 24 hrs. | 48 hrs. | C. neoformans 48 hours | A. fumigatus 48 hours |
| 1 | <0.32 | 3.60 | <0.32 | 3.90 |
| 21 | <0.32 | 1.30 | <0.32 | 4.10 |
| 24 | <0.32 | 1,40 | <0.32 | 1.90 |
| 29a | <0.32 | 1,10 | <0.32 | 0.37 |
| 34 | 1.6 | 6,50 | <0.32 | 3.90 |

The compounds of formula I and their pharmaceutically acceptable acid addition salts can be used as medicaments, e.g. in the form of pharmaceutical preparations for enteral, parenteral or topical administration. They can be administered, for example, perorally, such as in the form of tablets, coated tablets, dragées, hard and soft gelatine capsules, solutions, emulsions or suspensions, rectally, such as in the form of suppositories, parenterally, such as in the form of injection solutions or infusion solutions, or topically, such as in the form of ointments, creams or oils.

The production of the pharmaceutical preparations can be effected in a manner which will be familiar to any person skilled in the art by bringing the described compounds of formula I and their pharmaceutically acceptable acid addition salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the pathogenic fungi to be controlled, the age and the individual condition of the patient and the mode of administration, and will, of course, be fitted to the individual requirements in each particular case. For adult patients a daily dosage of about 0.01 g to about 4 g, especially about 0.05 g to about 2 g, comes into consideration for the prevention and control of topical and systemic infections by pathogenic fungi. For cholesterol lowering the daily dosage conveniently amounts to between 1 and 1200 mg, preferably 5 to 100 mg, for adult patients. Depending on the dosage it is convenient to administer the daily dosage in several dosage units.

The pharmaceutical preparations conveniently contain about 1–500 mg, preferably 2–200 mg, of a compound of formula I.

The following Examples serve to illustrate the present invention in more detail. They are, however, not intended to limit its scope in any manner. All temperatures are given in degrees Celcius.

EXAMPLE A

Aa) 30 ml of nitrobenzene are cooled in an ice bath and treated in succession at a maximum 6° C. with 6.6 g of aluminium chloride and 10.95 g of 4-bromo-2-fluoro-benzoyl chloride (prepared from 10 g of 4-bromo-2-fluoro-benzoic acid and 4.34 ml of oxalyl chloride in methylene chloride with 5 drops of DMF as the catalyst) in 20 ml of nitrobenzene. The mixture is stirred, whereafter 4.5 ml of anisole are added in such a manner that the temperature does not rise above 6° C. The solution is left to warm to room temperature overnight, poured on to ice-water and extracted with methylene chloride. The organic phase is washed with water and 10% sodium chloride solution, dried over sodium sulphate and concentrated. After crystallization from cyclohexane there are obtained 1 1.3 g of (4-bromo-2-fluoro-phenyl)-(4-methoxy-phenyl)-methanone, m.p. 93°–94° C.

Ab) A solution of 11.14 g of the product from Aa) in 70 ml of acetic acid and 50 ml 62% aqueous HBr solution is boiled under reflux, subsequently evaporated, re-evaporated with toluene and taken up in ethyl acetate. The organic phase is washed with saturated sodium hydrogen carbonate solution and 10% sodium chloride solution and dried. There are obtained 10.5 g of (4-bromo-2-fluoro-phenyl)-(4-hydroxy-phenyl)-methanone, MS: m/e 294 (M,1 Br).

Ac) 5.25 g of the product from Ab) are taken up in 170 ml of acetone and treated with 7.35 g of potassium carbonate and 8.13 ml of 1,6-dibromohexane. The suspension is heated under reflux for 4 hrs., then cooled, filtered and concentrated. After removal of the excess 1,6-dibromohexane and crystallization from cyclohexane 4.25 g of [4-[6-bromo-hexyloxy]-phenyl]-(4-bromo-2-fluoro-phenyl)methanone are obtained.

Ad) 4.1 g thereof are taken up in 30 ml of dimethylacetamide (DMA), treated at 0° C. with 1.77 ml of N-allyl-methyl-amine, again treated with 1.77 ml of N-allyl-methylamine after one day and, after an additional 30 min., concentrated. The residual oil is taken up in methylene chloride, washed with saturated sodium hydrogen carbonate and dried. The [4-[6-(allyl-methyl-amino)-hexyloxyl]-phenyl]-(4-bromo-2-fluoro-phenyl)-methanone obtained after purification on silica gel with methylene chloride:methanol (95:5) is taken up in ethanol and treated with 1.45 g of fumaric acid. The homogeneous solution is evaporated and dried. There is obtained [4-[6-(allyl-methyl-amino)-hexyloxy]-phenyl]-(4-bromo-2-fluoro-phenyl)-methanone.fumarate (1:1) as a sticky oil, MS: m/e 447 (M, 1 Br).

EXAMPLE B

Analogously to Ac) and Ad), from 2-fluoro-4-hydroxy-acetophenone via 1-[4-[6- bromo-hexyloxy]-2-fluoro-pheny]-ethanone there is obtained 1-[4-[6-(allyl-methyl-amino)-hexyloxy]-2-fluoro-pheny]-ethanone which is converted into the fumarate, MS: m/e 308 (M+H$^+$).

EXAMPLE 1

Allyl-[6-[3-(4-bromo-phenyl)-benzo[d]isothiazol-6-yloxy]-hexyl]-methyl-amine a) 4.3 g of potassium tert. butylate are dissolved in 160 ml of THF and treated slowly with 4.5 ml of benzyl mercaptan. The suspension is stirred at RT and then treated with 10 g of (4-bromophenyl)-(2-fluoro-4-methoxy-phenyl)-methanone in 200 ml of THF. The solution is stirred at RT and treated with 100 ml of ammonium chloride solution as well as 200 ml of sodium hydrogen carbonate solution. The phases are separated, the inorganic phase is extracted with ethyl acetate and the organic phases are washed with sat. sodium hydrogen carbonate solution and sodium chloride solution and dried. There are obtained 15.8 g of (2-benzylsulphanyl-4-methoxyphenyl)-(4-bromo-phenyl)-methanone which are taken up in 160 ml of methylene chloride, treated with 3.4 ml of sulphuryl chloride and stirred at RT. After distillation of the sulphuryl chloride the residue is taken up in 160 ml of THF, treated with 120 ml of a saturated ammonia solution in ethanol and stirred. 100 ml of sodium hydrogen carbonate solution are added. The solvent is removed and the residue is again taken up in sodium hydrogen carbonate solution and ethyl acetate. The phases are separated and the inorganic phase is extracted with ethyl acetate and ether. The organic phases are washed with sodium chloride solution and dried. Recrystallization from ethyl acetate/ethanol yields 7.52 g of 3-(4-bromo-phenyl)-6-methoxy-[d]-benzisothiazole, MS: m/e 318 (M, 1 Br).

b) 6.32 g of the product from a) are dissolved in 395 ml of methylene chloride, cooled to −78° C. and treated with 49.3 ml of boron tribromide solution (1M in methylene chloride). The solution is thawed overnight and then stirred at RT. The solution is added to sodium hydrogen carbonate solution, the phases are separated and the aqueous phase is extracted with 150 ml of methylene chloride. The organic phases are washed with sodium chloride solution and dried. 1.5 g of (4-bromo-phenyl)-benzo[d]isothiazol-6-ol from methylene chloride are crystallized from the crude product using methylene chloride. The mother liquor is concentrated, dissolved in 320 ml of methylene chloride and treated at −78° C. with 40 ml of boron tribromide solution (1M in methylene chloride). After working-up and crystallization there are obtained a further 2.24 g of 3-(4-bromo-phenyl)-benzo[d]isothiazol-6-ol.

c) 3.0 g of the product from b) are dissolved in 50 ml of acetone under argon and treated with 8.73 g of potassium carbonate and 3.85 ml of 1,6-dibromohexane. The suspension is heated under reflux, then cooled, treated with methylene chloride and filtered. The residue is washed. The mixture is concentrated and the residue is taken up in methylene chloride and dried. The crude product is concentrated and freed from excess 1,6-dibromohexane. 4.18 g of 6-(6-bromo-hexyloxy)-3-(4-bromo-phenyl)-benzo[d]isothiazole are obtained as a pale brown substance.

d) 4.15 g of the product from c) are taken up in 40 ml of DMA and treated under argon with 2.6 ml of N-allyl-methyl-amine and stirred at RT. A further 1.7 ml of N-allyl-methyl-amine are added and the mixture is stirred under argon. The solvent and the excess N-allyl-methyl-amine are removed. The crude product is taken up in methylene chloride, washed with sat. sodium hydrogen carbonate solution and sodium chloride solution and dried. The crude produce is purified by column chromatography (silica gel, methylene chloride:methanol (95:5). 3.02 of allyl-[6-[3-(4-bromo-phenyl)-benzo[d]isothiazol-6-yloxy]-hexyl]-methyl-amine are obtained as a yellow oil. This is dissolved in 50 ml of ethanol and 7 ml of methylene chloride and treated with 750 mg of fumaric acid in 20 ml of ethanol. The solution is concentrated, the substance is again taken up in 25 ml of ethyl acetate and 3 ml of ethanol, the solution is heated to 60° C., then cooled and crystallized. There are obtained 3.43 g of colourless allyl-[6-[3-(4-bromo-phenyl)-benzo[d]isothiazol-6-yloxy]-hexyl]-methyl-amine.fumarate (1:1), melting point 122°–123.5° C., MS: m/e 459 (M+H$^+$, 1 Br).

EXAMPLE 2

Analogously to Example 1:

a) from 3-(4-bromo-phenyl)-6-methoxy-[d]-benzisothiazole (Ex. 1a), after cleavage of the methoxy protecting group, reaction with (E)-1,4-dibromobutene and N-allyl-methyl-amine and salt formation, via 3-(4-bromo-phenyl)-benzo[d]isothiazol-6-ol and via (E)-6-(4-bromo-but-2-enyloxy)-3-(4-bromo-phenyl)-benzo[d]isothiazole there is obtained (E)-allyl-[4-[3-(4-bromo-phenyl)-benzo[d]isothiazol-6-yloxy]-but-2-enyl]-methyl-amine.fumarate (1:1), MS: m/e 429 (M+H$^+$, 1 Br), b) from 3-(4-bromo-phenyl)-6-methoxy-[d]-benzisothiazole (Ex. 1a), after cleavage of the methoxy protecting group, reaction with 1,6-dibromohexane and methyl-(2-methylsulphanyl-ethyl)-amine and salt formation, via 3-(4-bromo-phenyl)-benzo[d]isothiazol-6-ol and via 6-(6-bromo-hexyloxy)-3-(4-bromo-phenyl)-benzo[d]isothiazole there is obtained 6-[3-(4-bromo-phenyl)-benzo[d]isothiazol-6-yloxy]-hexyl]-methyl-(2-methylsulphanyl-ethyl)-amine.fumarate (1:1), MS: m/e 431 (M—$C_2H_5S^+$, 1 Br), c) from 3-(4-bromo-phenyl)-6-methoxy-[d]-benzisothiazole (Ex. 1a), after cleavage of the methoxy protecting group, reaction with (E)-1,4-dibromobutene and methyl-(2-methylsulphanyl-ethyl)-amine and salt formation, via 3-(4-bromo-phenyl)-benzo[d]isothiazol-6-ol and via (E)-6-(4-bromo-but-2-enyloxy)-3-(4-bromo-phenyl)-benzo[d]isothiazole there is obtained (E)-[4-[3-(4-bromo-phenyl)benzo[d]isothiazol-6-yloxy]-but-2-enyl]-methyl-(2-methylsulphanyl-ethyl)-amine.fumarate (1:1), MS: m/e 401 (M—$C_2H_5S^+$, 1 Br), d) from 2-fluoro-4-methoxyacetophenone with benzyl mercaptan, sulphuryl chloride and ammonia in ethanol, via 1-(2-benzyl-sulphanyl-4-methoxy-phenyl)-ethanone there is obtained 6-methoxy-3-methyl-benzo[d]isothiazole, m.p. 75°–76° C., MS: m/e 179 ($M^{30}$), and, after cleavage of the methoxy protecting group, reaction with 1,6-dibromohexane and N-allyl-methyl-amine and salt formation, via 3-methyl-benzo[d]isothiazol-6-ol and via 6-(6-bromo-hexyloxy)-3-methyl-benzo[d]isothiazole there is obtained allyl-methyl-[6-(3-methyl-benzo[d]isothiazol-6-yloxy)-hexyl]-amine.fumarate (1:1), MS: m/e 318 (M), e) from 6-methoxy-3-methyl-benzo[d]isothiazole (intermediate in Ex. 2d), after cleavage of the methoxy protecting group, reaction with (E)-1,4-dibromobutene and N-allyl-methyl-amine and salt formation, via 3-methyl-benzo[d]isothiazol-6-ol and via (E)-6-(4-bromo-but-2-enyloxy)-3-methyl-benzo[d]isothiazole there is obtained (E)-allyl-methyl-[4-(3-methyl-benzo[d]isothiazol-6-yloxy)-but-2-enyl]-amine.fumarate (1:1), MS: m/e 289 ($M+H^+$), f) from (4-bromo-2-fluoro-phenyl)-(4-methoxy-phenyl)-methanone (Ex. Aa), via (2-benzylsulphanyl-4-bromo-phenyl)-(4-methoxy-phenyl)-methanone and via 6-bromo-3-(4-methoxyphenyl)-[d]-benzoisothiazole, MS: m/e 319 (M, 1 Br), and after cleavage of the methoxy protecting group, reaction with 1,6-dibromohexane and N-allyl-methyl-amine and salt formation, via 4-(6-bromo-benzo[d]isothiazol-3-yl)-phenol and via 6-bromo-3-[4-(6-bromo-hexyloxy)-phenyl]-benzo[d]isothiazole there is obtained allyl-[6-[4-(6-bromo-benzo[d]isothiazol-3-yl)-phenoxy]-hexyl]-methyl-amine.fumarate (1:1), MS: m/e 458 (M, 1 Br), g) from 6-bromo-3-(4-methoxy-phenyl)-[d]-benzoisothiazole (intermediate in Ex. 2f), after cleavage of the methoxy protecting group, reaction with (E)-1,4-dibromobutene and N-allyl-methyl-amine and salt formation, via 4-(6-bromo-benzo[d]isothiazol-3-yl)-phenol and via (E)-6-bromo-3-[4-(4-bromo-but-2-enyloxy)-phenyl]-benzo[d]isothiazole there is obtained (E)-allyl-[4-[4-(6-bromo-benzo[d]isothiazol-3-yl)-phenoxy]-but-2-enyl]-methyl-amine.fumarate (1:1), m.p. 125°–125.5° C.

EXAMPLE 3

Allyl-[6-[3-(4-bromo-phenyl)-benzo[b]thiophen-6-yloxy]-hexyl]methyl-amine a) 1.45 g of NaSMe (95%) are suspended in 80 ml of THF and treated over a period of 1.5 h. with 5.51 g of (4-bromo-phenyl)-(2-fluoro-4-methoxy-phenyl)-methanone in 100 ml of THF. The solution is stirred at RT, again treated with 264 mg of NaSMe, stirred and treated after an interval of 10 min. with 50 ml of sat. $NH_4Cl$ solution and 100 ml of sodium hydrogen carbonate solution. The inorganic phase is extracted with $CH_2Cl_2$ and the organic phases are washed with sat. sodium hydrogen carbonate solution as well as sodium chloride solution and dried. The crude product is purified by column chromatography (silica gel, ethyl acetate:hexane 1:2). 5.88 g of (4-bromo-phenyl)-(4-methoxy-2-methylsulphanyl-phenyl)-methanone are obtained as a yellow oil.

b) 2.55 g of potassium tert. butylate are placed in 15 ml of THF and treated with 2.50 g of the product from a) in 12 ml of THF. The mixture is heated under reflux and then treated with water and $NH_4Cl$. The inorganic phases are extracted with ethyl acetate. The organic phases are washed with saturated sodium hydrogen carbonate solution and sodium chloride solution and dried. The crude product obtained after concentration (2.08 g) is dissolved in 14 ml of toluene and treated with 6 ml of trifluoroacetic acid at 0° C. The mixture is neutralized with saturated sodium hydrogen carbonate solution. The inorganic phase is extracted with ethyl acetate. The organic phases are washed with sat. sodium hydrogen carbonate solution and sodium chloride solution and dried. The crude product obtained is purified by column chromatography (silica gel, ethyl acetate:hexane 1:6) and crystallized from ethyl acetate:hexane. There are obtained 476 mg of 3-(4-bromo-phenyl)-6-methoxy-benzo[b]thiophene as white crystals, m.p. 102.5°–104.5° C., MS: m/e 318 (M, Br).

c) From 3-(4-bromo-phenyl)-6-methoxy-benzo[b]thiophene, after cleavage of the methoxy protecting group (analogously to Ex. Ab), reaction with 1,6-dibromohexane (analogously to Ex. Ac) and N-allyl-methyl-amine and salt formation (analogously to Ex. Ad), via 3-(4-bromo-phenyl)-benzo[b]thiophen-6-ol and via 6-(6-bromo-hexyloxy)-3-(4-bromo-phenyl)-benzo[b]thiophene there is obtained allyl-[6-[3-(4-bromo-phenyl)-benzo[b]thiophen-6-yloxy]-hexyl]methyl-amine.fumarate (1:1), MS: m/e 457 ($M+H^{30}$, Br).

EXAMPLE 4

Analogously to Example 3, from 3-(4-bromo-phenyl)-6-methoxy-benzo[b]thiophene (Ex. 3b), after cleavage of the methoxy protecting group, reaction with (E)-1,4-dibromobutene and N-allyl-methyl-amine and salt formation, via 3-(4-bromo-phenyl)-benzo[b]thiophen-6-ol und via 6-(4-(E)-bromo-but-2-enyloxy)-3-(4-bromo-phenyl)-benzo[b]thiophene there is obtained (E)-allyl-[4-[3(4-bromo-phenyl)-benzo[b]thiopen-6-yloxy]-but-2-enyl]-methyl-amine.fumarat (1:1), MS: m/e 428 ($M+H^+$, Br).

EXAMPLE 5

Allyl-methyl-[6-[3-(4-methyl-pent-3-enyl)-benzo[d]isothiazol-6-yloxy]-hexyl-amine 105 mg of allyl-methyl-[6-(3-methyl-benzo[d]isothiazol-6-yloxy)-hexyl]-amine (Ex. 2d) in 2 ml of THF are added dropwise over a period of 20 min. at −78° C. to a lithium diisopropylamide (LDA) solution previously prepared from 100 µl of diisopropylamine and 425 µl of n-butyllithium (1.6M in hexane) in 2 ml of THF. The mixture is stirred at −78° C., treated with 3,3-dimethylallyl bromide and thawed overnight. For the working-up, the mixture is again cooled to −78° C. and treated with 42 µl of acetic acid in 0.3 ml of ether. The mixture is added to ice-cold sodium hydrogen carbonate solution and the inorganic phase is extracted with methylene chloride. The organic phases are washed with sodium chloride solution and dried. The crude product obtained after concentration is purified by column chromatography (silica gel, $CH_2Cl_2$:MeOH:$NH_4OH$ 95:5:0.5). 63 mg of allyl-methyl-[6-[3-(4-methyl-pent-3-enyl)-benzo[d]isothiazol-6-yloxyl-hexyl-amine are obtained. This is taken up in 2 ml of ethanol and treated with 18.1 mg of fumaric acid. After stirring the solvent is removed and the residue is lyophilized. There are obtained 80 mg of allyl-methyl-[6-[3-(4-methyl-pent-3-enyl)-benzo[d]isothiazol-6-yloxy]-hexyl-amine.fumarate (1:1), MS: m/e 357 (M+H⁺).

EXAMPLE 6

Analogously to Example 5, from (E)-allyl-methyl-[4-(3-methyl-benzo [d]isothiazol-6-yloxy)-but-2-enyl]-amine (Ex. 2e) and 3,3-dimethylallyl bromide with LDA in THF and subsequent salt formation there is obtained (E)-allyl-methyl-[4-[3-(4-methyl-pent-3-enyl)-benzo[d]isothiazol-6-yloxy]-but-2-enyl]-amine.fumarate (1:1), MS: m/e 357 (M+H⁺).

EXAMPLE 7

(E)-Allyl-methyl-[6-[3-(4-methyl-penta-1,3-dienyl)-benzo[d]isothiazol-6-yloxy]-hexyl]-amine a) 7.0 g of 6-methoxy-3-methyl-benzo[d]isothiazole (intermediate in Example 2d) are dissolved in 77 ml of acetic acid and treated with 45 ml of 62% aqueous HBr and heated to 125° C. overnight. The solution is treated with sodium hydrogen carbonate solution. The inorganic phase is extracted with ethyl acetate and the organic phases are washed with sodium hydrogen carbonate solution and sodium chloride solution and dried. 5.12 g of 3-methyl-benzo[d]isothiazol-6-ol are crystallized from $CH_2Cl_2$.

b) 1.5 g of 3-methyl-benzo[d]isothiazol-6-ol in 26 ml of THF are added to a LDA solution previously prepared from 3.9 ml of diisopropylamine and 16.0 ml of n-butyllithium (1.6M in hexane) in 23 ml of THF and the mixture is stirred at −78° C. 2.5 ml of 3-methyl-2-butenal in 40 ml of THF are added. The reaction mixture is thawed overnight and neutralized with 3.9 ml of acetic acid in 20 ml of ether. The mixture is added to sodium hydrogen carbonate solution, the inorganic phase is extracted with ethyl acetate and the organic phases are washed with sodium chloride solution and dried. The crude product is purified by chromatography (silica gel, ethyl acetate:hexane 1:1). 1.5 g of (RS)-3-(2-hydroxy-4-methyl-pent-3-enyl)-benzo[d]isothiazol-6-ol are obtained.

c) 308 mg of the product from b) in a 1:1 mixture of toluene and THF are treated with 285 mg of p-toluenesulphonic acid in 7 ml of toluene. After a further 48 h. additional p-toluenesulphonic acid is added and the reaction mixture is heated to 60° C. for 6 h. After the addition of water the inorganic phase is extracted with ethyl acetate. The organic phases are washed with sodium hydrogen carbonate solution and sodium chloride solution and dried. There are obtained 296 mg of a mixture of 3-(4-methyl-penta-2,4-dienyl)benzo[d]isothiazol-6-ol and 3-(4-methyl-penta-1,3-dienyl)benzo[d]isothiazol-6-ol, MS: m/e 357 (M+H⁺).

d) 307 mg of the product from c) are dissolved in 12 ml of toluene, treated with 1 ml of trifluoroacetic acid and stirred at 60° C. The reaction solution is poured into sodium carbonate solution, the inorganic phase is extracted with ethyl acetate and the organic phases are washed with sodium hydrogen carbonate solution and sodium chloride solution and dried. The crude product is purified by chromatography (silica gel, ethyl acetate: hexane 1:2). 190 mg of 3-(4-methyl-penta-1,3-dienyl)-benzo[d]isothiazol-6-ol are obtained.

e) From the product from c) with 1,6-dibromohexane (analogously to Ex. 1c) and N-allyl-methyl-amine and salt formation (analogously to Ex. 1d) via 6-(6-bromo-hexyloxy)-3-(4-methyl-penta-1,3-dienyl)-benzo[d]isothiazole there is obtained (E)-allyl-methyl-[6-[3-(4-methyl-penta-1,3-dienyl)-benzo[d]isothiazol-6-yloxy]-hexyl]amine.fumarate (1:1), MS: m/e 385 (M+H⁺).

EXAMPLE 8

Analogously to Example 7:

a) From (RS)-3-(2-hydroxy-4-methyl-pent-3-enyl)-benzo[d]isothiazol-6-ol (Ex. 7b) with 1,6-dibromohexane and N-allyl-methyl-amine and salt formation (analogously to Ex. 1d) via (RS)-1-[6-(6-bromo-hexyloxy)-benzo[d]isothiazol-3-yl]-4-methyl-pent-3-en-2-ol there is obtained (RS)-1-[6-[6-(allyl-methyl-amino)-hexyloxy]-benzo[d]isothiazol-3-yl]-4-methyl-pent-3-en-2-ol.fumarate (1:1), MS: m/e 403 (M+H⁺), b) from (RS)-3-(2-hydroxy-4-methyl-pent-3-enyl)-benzo[d]isothiazol-6-ol (Ex. 7b) with (E)-1,4-dibromobutene and N-allyl-methyl-amine via (E)-1-[6-(4-bromo-but-2-enyloxy)-benzo[d]isothiazol-3-yl]-4-methyl-pent-3-en-2-ol there is obtained (E)-(RS)-1-[6-[4-(allyl-methyl-amino)-but-2-enyloxy]-benzo[d]isothiazol-3-yl]-4-methyl-pent-3-en-2-ol, MS: m/e 373 (M+H⁺).

c) From 3-(4-methyl-penta-2,4-dienyl)-benzo[d]isothiazol-6-ol and 3-(4-methyl-penta-1,3-dienyl)-benzo[d]isothiazol-6-ol (Ex. 7c) with (E)-1,4-dibromobutene and N-allyl-methyl-amine via 6-(4-bromo-but-2-enyloxy)-3-(4-methyl-penta-1,3-dienyl)-benzo[d]isothiazole and 6-(4-bromo-but-2-enyloxy)-3-(4-methyl-penta-2,4-dienyl)-benzo[d]isothiazole there is obtained a 7:3 mixture of allyl-methyl-[(E)-4-[3-[(E)-4-methyl-penta-2,4-dienyl]benzo[d]isothiazol-6-yloxy]-but-2-enyl]-amine and allyl-methyl-[(E)-4-[3-[(E)-4-methyl-penta-1,3-dienyl]-benzo[d]isothiazol-6-yloxy]-but-2-enyl]-amine, MS: m/e 355 (M+H⁺).

EXAMPLE 9

7:3 Mixture of (E)-allyl-methyl-[6-[3-(4-methyl-penta-2,4-dienyl)-benzo[d]isothiazol-6-yloxyl]-hexyl]-amine and (E)-allyl-methyl-[6-[3-(4-methyl-penta-1,3-dienyl)-benzo[d]isothiazol-6-yloxy]-hexyl]-amine 116 mg of p-toluenesulphonic acid are added to 97 mg of (RS)-1-[6-[6-(allyl-methyl-amino)-hexyloxy)-benzo[d]isothiazol-3-yl]-4-methyl-pent-3-en-2-ol (Ex. 8a) in 7 ml of toluene and 5 ml of THF and, after stirring overnight, a further 92 mg of p-toluenesulphonic acid are added. The reaction mixture is stirred further, then concentrated and treated with water. The inorganic phase is extracted with methylene chloride. The organic extracts are washed with sodium hydrogen carbonate solution and sodium chloride solution and dried. The crude product obtained is purified by column chromatography (silica gel, $CH_2Cl_2$:MeOH). 75 mg of the title mixture are obtained, MS: m/e 385 (M+H⁺).

EXAMPLE 10

Allyl-[6-[3-(4-bromo-1,1-dioxo-benzo[d]isothiazol-6-yloxy]-hexyl]-methyl-amine a) 650 mg of 6-(6-bromo-hexyloxy)-3-(4-bromo-phenyl)-benzo[d]isothiazole (Ex. 1c) are taken up in 60 ml of methylene chloride and treated with 3 g of potassium permanganate (on silica gel). The suspension is stirred at RT, then treated with sodium sulphate and filtered over silica gel. After concentration 439 mg of 6-(6-bromo-hexyloxy)-3-(4-bromo-phenyl)-benzo[d]isothiazole 1,1-dioxide, MS: m/e 499 (M, 1 Br), are crystallized from ethyl acetate, hexane and methylene chloride.

b) From the product of a) and N-allyl-methyl-amine and after salt formation there is obtained (analogously to Ex. 1d) allyl-[6-[3-(4-bromo-phenyl)-1,1-dioxo-benzo[d]isothiazol-6-yloxy]-hexyl]-methyl-amine.fumarate (1:1), MS: m/e 491 (M+H$^+$, 1 Br).

EXAMPLE 11

Analogously to Example 10, from 6-bromo-3-[4-(6-bromo-hexyloxy)-phenyl]-benzo[d]isothiazole (intermediate from Ex. 2f) after oxidation with KMnO$_4$ there is obtained 6-bromo-3-[4-(6-bromo-hexyloxy)-phenyl]-benzo[d]isothiazole 1,1-dioxide which with N-allyl-methyl-amine and after salt formation (analogously to Ex. 1d) gives allyl-[6-[4-(6-bromo-1,1-dioxo-benzo[d]isothiazol-3-yl)-phenoxy]-hexyl]-methyl-amine.fumarate (1:1), MS: m/e 491 (M+H$^+$, 1 Br).

EXAMPLE 12 a) A mixture of 4.25 g of (4-bromo-phenyl)-(2,4-dihydroxyphenyl)-methanone, 3.22 g of hydroxylamine.hydrochloride and 2.85 g of sodium acetate in 100 ml of ethanol is heated under reflux. The reaction mixture is concentrated, treated with 100 ml of saturated aqueous sodium hydrogen carbonate solution and extracted with ethyl acetate. The organic extracts are washed with saturated sodium chloride solution, dried and evaporated. The residue is treated with 200 ml of ethanol. After the addition of 1.1 g of p-toluenesulphonic acid the mixture is heated to 85° C. for 24 hrs. For the working-up, the reaction mixture is concentrated and the residue is taken up in 250 ml of ethyl acetate and washed with saturated sodium hydrogen carbonate solution and with saturated sodium chloride solution. The organic phase is dried and evaporated. There are obtained 4.0 g of 3-(4-bromo-phenyl)-benzo[d]isoxazol-6-ol, MS: m/e 289 (M+H$^+$, 1 Br).

b) Analogously to Example 1, from 3-(4-bromo-phenyl)-benzo[d]isoxazol-6-ol and (E)-1,4-dibromo-2-butene via (E)-6-(4-bromo-but-2-enyloxy)-3-(4-bromo-phenyl)-benzo[d]isoxazole and by reaction with N-allyl-methyl-amine there is obtained (E)-allyl-[4-[3-(4-bromo-phenyl)-benzo[d]isoxazol-6-yloxy]-but-2-enyl-methyl-amine which is converted into the fumarate, MS: m/e 412 (M$^{30}$, 1 Br).

EXAMPLE 13

Analogously to Example 12b, from 3-(4-bromo-phenyl)-benzo[d]isoxazol-6-ol and 1,6-dibromohexane via 6-(6-bromo-hexyloxy)-3-(4-bromo-phenyl)-benzo[d]isoxazole and by reaction with N-allyl-methyl-amine there is obtained allyl-[6-[3-(4-bromo-phenyl)-benzo[d]isoxazol-6-yloxy]-hexyl]-methyl-amine which is converted into the fumarate, MS: m/e 443 (M+H$^+$, 1 Br).

EXAMPLE 14 a) 7.2 g of aluminium chloride are added to 80 ml of nitrobenzene at 5° C. and a solution of 8 g of 4-bromo-2-chloro-benzoyl chloride in 20 ml of nitrobenzene is added dropwise in such a manner that the temperature does not exceed 10° C. After stirring and adding 3.26 ml of anisole the reaction mixture is warmed to room temperature, stirred and subsequently poured on to ice-water and extracted with methylene chloride. The extracts are washed with saturated sodium chloride solution, dried and evaporated. There are obtained 10.0 g of (4-bromo-2-chloro-phenyl)-(4-methoxy-phenyl)-methanone, MS: m/e 324 (M+H$^+$, 1 Br).

b) A mixture of 4.0 g of the product from a), 3.41 g of hydroxylamine.hydrochloride and 3.0 g of sodium acetate in 80 ml of ethanol is heated under reflux for 3 days. The reaction mixture is concentrated, treated with saturated sodium hydrogen carbonate solution and extracted with ethyl acetate. The organic extracts are washed with saturated sodium chloride solution, dried and evaporated. The residue is taken up in dimethylacetamide and treated with 7.1 g of potassium carbonate. After stirring at 120° C. and after cooling the reaction mixture is filtered. The filtrate is concentrated and the residue is purified by chromatography (silica gel, ethyl acetate/hexane 1:9 to 2:8). There are obtained 3.5 g of 6-bromo-3-(4-methoxy-phenyl)-benzo[d]isoxazole, MS: m/e 303 (M+H$^+$, 1 Br).

c) A mixture of 3.4 g of the product from b), 80 ml of acetic acid and 50 ml of 62% aqueous hydrobromide solution is stirred at 95° C. for 8 hrs., subsequently evaporated, taken up in ethyl acetate, poured into saturated sodium hydrogen carbonate solution and extracted with ethyl acetate. The organic phases are washed with saturated sodium chloride solution, dried and evaporated. After chromatography of the residue (silica gel, ethyl acetate/hexane 3:7) there are obtained 2.7 g of 4-(6-bromo-benzo[d]isoxazol-3-yl)phenol, MS: m/e 289 (M+H$^+$, 1 Br).

d) Analogously to Example 1, from 4-(6-bromo-benzo[d]isoxazol3-yl)-phenol and 1,6-dibromohexane via 6-bromo-3-[4-(6-bromo-hexyloxy)-phenyl]-benzo[d]isoxazole and by reaction with N-allyl-methyl-amine there is obtained allyl-[6-[4-(6-bromo-benzo[d]-isoxazol-3-yl)-phenoxy]-hexyl-methyl-amine which is converted into the fumarate, MS: m/e 442 (M+H$^+$, 1 Br).

EXAMPLE 15

Analogously to Example 14d, from 4-(6-bromo-benzo[d]isoxazol-3-yl)-phenol and (E)-1,4-dibromo-2-butene via (E)-6-bromo-3-[4-(4-bromo-but-2-enyloxy)-phenyl]-benzo[d]isoxazole and by reaction with N-allyl-methyl-amine there is obtained (E)-allyl-[4-[4-(6-bromo-benzo[d]isoxazol-3-yl)-phenoxy]-but-2-enyl]-methyl-amine which is converted into the fumarate, MS: m/e 413 (M+H$^+$, 1 Br).

EXAMPLE 16

A mixture of 0.15 g of (4-bromo-phenyl)-[4-[6-(cyclopropyl-methyl-amino)-hexyloxy]-2-fluoro-phenyl]-methanone, 0.17 g of hydroxylamine.hydrochloride and 0.20 g of sodium acetate in 14 ml of ethanol is heated to 90° C. for 32 hrs. and then concentrated. The residue (containing the oxime corresponding to the starting ketone) is taken up in 50 ml of methylene chloride and washed with saturated aqueous sodium hydrogen carbonate solution and sodium chloride solution. The organic phase is dried and evaporated. The residue is dissolved in 15 ml of DMA and treated with 0.22 g of potassium carbonate. The mixture is heated at 130° C. for 5 hrs. For the working-up, the reaction mixture is filtered, the filtrate is concentrated and the residue is purified by chromatography (silica gel, toluene/acetone/triethylamine 92:7:1). There is obtained 0.077 g of [6-[3-(4-bromo-phenyl)-benzo[d]isoxazol-6-yloxy]hexyl]-cyclopropyl-methyl-amine which is converted into the fumarate, MS: m/e 443 (M+H$^+$, 1 Br).

The starting material, MS: m/e 447 (M, 1 Br), is obtained by reacting [4-(6-bromo-hexyloxy)-2-fluoro-phenyl]-(4-bromo-phenyl)-methanone with N-methyl-cyclopropyl-amine.hydrochloride

EXAMPLE 17

Analogously to Example 16, from (E)-1-[4-[(E)-4-(allyl-methyl-amino)-but-2-enyloxy]-2-fluoro-phenyl]-5-methyl- 4-hexen-1-one and hydroxylamine-hydrochloride and cyclization with potassium carbonate there is obtained (E)-allyl-methyl-[4-[3-(4-methyl-pent-3-enyl)-benzo[d]isoxazol-6-yloxy]-but-2-enyl]-amine which is converted into the fumarate, MS: m/e 341 (M).

The starting material is obtained as follows:

A solution of 52.0 ml of diisopropylamine in 600 ml of THF is treated dropwise at 0° C. with 230 ml of 1.6M butyllithium in hexane. After 1.5 hr. at 0° C. the mixture is cooled to −78° C. and treated dropwise with 26.8 g of 2-fluoro-4-hydroxyacetophenone in 120 ml of THF. After 1 hr. at −78° C. 23.7 ml of 3,3-dimethylallyl bromide in 24 ml of THF are added dropwise. The mixture is left to warm to room temperature, whereupon 34 ml of acetic acid in 100 ml of ether are sprayed in at −78° C. The solution is poured into saturated ammonium chloride solution/ether and washed with 10% sodium chloride solution. After drying and evaporating the organic phase 33.8 g of 1-(2-fluoro-4-hydroxy-phenyl)-5-methyl-hex-4-en-1-one, m.p. 100°–101° C., are obtained from ether/pentane. By reacting this compound with (E)-1,4-dibromo-2-butene and then with N-allyl-methyl-amine there is obtained (E)-1-[4-[(E)-4-(allyl-methyl-amine)-but-2-enyloxy]-2-fluoro-phenyl]-5-methyl-4-hexen-1-one, MS: m/e 345 (M).

EXAMPLE 18 a) 11.5 g of 4-bromophenacyl bromide are dissolved in 250 ml of acetone and, after the addition of 5.75 g of potassium carbonate and 4.5 ml of 3-methoxyphenol, the reaction mixture is stirred and subsequently filtered. The filtrate is concentrated and the residue is chromatographed over silica gel with ethyl acetate/hexane (5:95 to 10:90). There are obtained 7.3 g of 1-(4-bromo-phenyl)-2-(3-methoxy-phenoxy)-ethanone, MS: m/e 320 (M+, 1 Br).

b) 5.0 g of the product from a) are treated with 53 g of polyphosphoric acid and heated to 80° C. For the working-up, the mixture is adjusted to pH~8 with saturated sodium carbonate solution, then cooled and subsequently extracted with ethyl acetate. The organic extracts are dried and concentrated. There are obtained 4.6 g of 3-(4-bromo-phenyl)-6-methoxy-benzofuran, MS: m/e 302 (M+, 1 Br).

c) 3.0 g of 3-(4-bromo-phenyl)-6-methoxy-benzofuran are treated at 0° C. with 100 ml of 1M boron tribromide solution in methylene chloride. The ice bath is removed and the reaction mixture is stirred, subsequently poured into saturated sodium carbonate solution and extracted with methylene chloride. The organic phases are washed with saturated sodium chloride solution, dried and evaporated. There are obtained 2.9 g of 3-(4-bromo-phenyl)-benzofuran-6-ol, MS: m/e 288 (M+, 1 Br).

d) Analogously to Example 1, from 3-(4-bromo-phenyl)benzofuran-6-ol and (E)-1,4-dibromo-2-butene via (E)-6-(4-bromo-but-2-enyloxy)-3-(4-bromo-phenyl)-benzofuran and by reaction with N-allyl-methyl-amine there is obtained (E)-allyl-[4-[3-(4-bromo-phenyl)-benzofuran-6-yloxy]-but-2-enyl]-methyl-amine which is converted into the fumarate, MS: m/e 412 (M+H+, 1 Br).

EXAMPLE 19

Analogously to Example 18d, from 3-(4-bromo-phenyl)-benzofuran-6-ol and 1,6-dibromohexane via 6-(6-bromo-hexyloxy)-3-(4-bromo-phenyl)-benzofuran and by reaction with N-allyl-methyl-amine there is obtained allyl-[6-[3-(4-bromo-phenyl)-benzofuran-6-yloxy]-hexyl]-methyl-amine which is converted into the fumarate, MS: m/e 442 (M+H+, 1 Br).

EXAMPLE 20 a) 29.2 ml of 2-(4-methoxyphenyl)-ethylamine and 34.2 ml of diisopropylethylamine are added dropwise in succession at 0° C. to a solution of 43.9 g of 4-bromobenzoyl chloride in 500 ml of methylene chloride. The reaction mixture is left to warm to room temperature and stirred, subsequently diluted with methylene chloride and treated with saturated sodium hydrogen carbonate solution. The organic phase is washed with saturated sodium hydrogen carbonate solution and then saturated sodium chloride solution, dried and concentrated. There are obtained 66.1 g of 4-bromo-N-[2-(3-methoxy-phenyl)-ethyl]-benzamide, MS: m/e 333 (M+, 1 Br).

b) 50 g of 4-bromo-N-[2-(3-methoxy-phenyl)-ethyl]-benzamide are dissolved in 750 ml of acetonitrile and treated under argon with 55 ml of phosphorus oxychloride. After heating to 80° C. the majority of the solvent is removed and the residue is adjusted to pH >12 with concentrated ammonia solution and extracted with ethyl acetate. The organic extracts are washed with saturated sodium chloride solution, dried and concentrated. There are obtained 46.4 g of 1-(4-bromo-phenyl)-6-methoxy-3,4-dihydro-isoquinoline, MS: m/e 314 (M+, 1 Br).

c) Cleavage of the methoxy protecting group (analogously to Ex. 14c) from 1-(4-bromo-phenyl)-6-methoxy-3,4-dihydro-isoquinoline (15 g) is effected with 95 ml of acetic acid and 65 ml of 62% aqueous hydrobromide solution at 100° C. and gives 13.7 g of 1-(4-bromo-phenyl)-3,4-dihydro-isoquinolin-6-ol, MS: m/e 301 (M+, 1 Br).

d) Analogously to Example 1, from 1-(4-bromo-phenyl)-3,4-dihydro-isoquinolin-6-ol and 1,6-dibromohexane there is obtained 6-(6-bromo-hexyloxy)-1-(4-bromo-phenyl)-3,4-dihydro-isoquinoline and, after reaction with N-allyl-methyl-amine, there is obtained allyl-[6-[1-(4-bromo-phenyl)-3,4-dihydro-isoquinolin-6-yloxy]-hexyl]-methyl-amine which is converted into the fumarate, MS: m/e 455 (M+H+, 1 Br).

EXAMPLE 21

0.3 g of allyl-[6-[1-(4-bromo-phenyl)-3,4-dihydro-isoquinolin-6-yloxy]-hexyl]-methyl-amine (Ex. 20d) is dissolved in 50 ml of ethanol and cooled to 0° C. using an ice bath. A total of 0.185 g of sodium borohydride is added in three portions within 10 minutes and the mixture is warmed to room temperature and stirred overnight. For the working-up, the reaction mixture is evaporated to a quarter and adjusted to pH~2 with 2M hydrochloric acid solution, again made basic with concentrated ammonia solution and extracted three times with methylene chloride. After evaporation of the organic extracts and chromatography of the residue on silica gel with toluene/acetone/triethylamine (50:49:1) as the eluent there is obtained 0.23 g of (RS)-allyl-[6-[1-(4-bromo-phenyl)-1,2,3,4-tetrahydro-isoquinolin-6-yloxy]-hexyl]-methyl-amine which is converted into the hydrochloride, MS: m/e 457 (M+H+, 1 Br).

EXAMPLE 22

0.1 g of (RS)-allyl-[6-[1-(4-bromo-phenyl)-1,2,3,4-tetra-hydro-isoquinolin-6-yloxy]-hexyl]-methyl-amine (Ex. 21) is taken up in 2 ml of a 1M NaH$_2$PO$_3$ solution and treated with 2 ml of dioxan as a solubilizer. After the addition of 2 ml of a 37% aqueous formaldehyde solution the mixture is heated to 65° C. for 48 hrs. For the working-up, the mixture is adjusted to pH >12 with 4M aqueous sodium hydroxide solution and extracted with ethyl acetate. After evaporation of the extracts and chromatography of the residue (silica gel, toluene/acetone/triethylamine, 25:74:1) there is obtained 0.12 g of (RS)-allyl-[6-[1-(4-bromo-phenyl)-2-methyl-1,2,3,4-tetrahydro-isoquinolin-6-yloxy]-hexyl]-methyl-amine which is converted into its hydrochloride, MS: m/e 471 (M+H$^+$, 1 Br).

EXAMPLE 23 a) 10 g of 1-(4-bromo-phenyl)-6-methoxy-3,4-dihydro-isoquinoline (Ex. 20b) are dissolved in in 500 ml of toluene, treated with 60 g of anhydrous sodium sulphate and 15 g of manganese dioxide and boiled under reflux for 24 hrs. After cooling the reaction mixture is filtered and concentrated.

b) The 1-(4-bromo-phenyl)-6-methoxy-isoquinoline obtained is boiled under reflux in 53 ml of acetic acid and 37 ml of 62% aqueous hydrobromic acid. Subsequently, after cooling to room temperature and addition of 150 ml of ethyl acetate the separated precipitate is filtered off. The crystals are washed with ethyl acetate and dried. There are obtained 7.6 g of 1-(4-bromo-phenyl)-isoquinolin-6-ol, MS: m/e 300 (M+H$^+$, 1 Br).

c) Analogously to Example 1, from 1-(4-bromo-phenyl)-isoquinolin-6-ol and 1,6-dibromohexane there is obtained 6-(6-bromo-hexyloxy)-1-(4-bromo-phenyl)-isoquinoline and after reaction with N-allyl-methyl-amine there is obtained allyl-[6-[1-(4-bromo-phenyl)-isoquinolin-6-yloxy]-hexyl]-methyl-amine, which is converted into the fumarate and the dihydrochloride, MS: m/e 453 (M+H$^+$, 1 Br).

EXAMPLE 24

Analogously to Example 23c, from 1-(4-bromo-phenyl)-isoquinolin-6-ol and 1,6-dibromohexane there is obtained 6-(6-bromo-hexyloxy)-1-(4-bromo-phenyl)-isoquinoline and after reaction with N-cyclopropyl-methyl-amine there is obtained [6-[1-(4-bromo-phenyl)-isoquinolin-6-yloxy]-hexyl]-cyclopropyl-methyl-amine which is converted into the fumarate, MS: m/e 453 (M+H$^+$, 1 Br).

EXAMPLE 25

A suspension of 0.5 g of 1-(4-bromo-phenyl)-isoquinolin-6-ol in 15 ml of DMF is cooled to 0° C. and treated with 0.15 g of ~55% sodium hydride. The mixture is stirred for 40 min., with a solution resulting. A solution of 0.39 g of (E)-1,4-dibromo-2-butene in 5 ml of DMF is added dropwise at −20° C. After stirring at −15° to −20° C. for 3 hrs. 0.8 ml of N-allyl-methyl-amine is added, the mixture is stirred overnight and warmed to room temperature. Subsequently, the reaction mixture is concentrated and the residue is treated with sodium hydrogen carbonate solution and extracted with methylene chloride. The organic extracts are washed with saturated sodium chloride solution, dried over sodium sulphate and concentrated. The residue is chromatographed with toluene/acetone/triethylamine (90:9:1 to 70:29:1). There is obtained 0.1 g of (E)-allyl-[4-[1-(4-bromo-phenyl)-isoquinolin-6-yloxy]-but-2-enyl]-methyl-amine which is converted into the fumarate, MS: m/e 423 (M+H$^+$, 1 Br).

EXAMPLE 26

Analogously to Example 25, from 1-(4-bromo-phenyl)-3,4-dihydro-isoquinolin-6-ol and (E)-1,4-dibromo-2-butene and after reaction with N-allyl-methyl-amine there is obtained (E)-allyl-[4-[1-(4-bromo-phenyl)-3,4-dihydro-isoquinolin-6-yloxy]-but-2-enyl]-methyl-amine, which is converted into the fumarate, MS: m/e 425 (M+H$^+$, 1 Br).

EXAMPLE 27 a) A solution of 3 g of (4-bromo-phenyl)-(2-methyl-4-methoxyphenyl)-methanone (prepared from 3-methylanisole and 4-bromobenzoyl chloride by Friedel-Crafts reaction analogously to Ex. 14a) in 100 ml of tetrachloromethane is treated with 2.1 g of N-bromosuccinimide and a spatula tip of dibenzoyl peroxide. The reaction mixture is stirred at room temperature for 6 hrs. under irradiation, subsequently diluted with 100 ml of methylene chloride and washed in succession with saturated sodium hydrogen carbonate solution and saturated sodium chloride solution. The organic phase is dried, filtered and immediately reacted. The solution is added dropwise to a mixture, previously stirred at 0° C., of 2.13 g of tert-butyl N-hydroxy-carbamate and 0.38 g of sodium hydride in 30 ml of TMF. The reaction mixture is warmed to room temperature and stirred. For the working-up, the mixture is treated with 60 ml of saturated ammonium chloride solution and the separated organic phase is washed with saturated sodium chloride solution, dried over sodium sulphate and concentrated. After chromatography of the residue (silica gel, ethyl acetate-hexane, 10:90 to 25:75) there are obtained 2.65 g of tert-butyl [2-(4-bromo-benzoyl)-5-methoxy-benzyloxy]-carbamate, MS: m/e 436 (M+H$^+$, 1 Br).

b) A solution of 1.9 g of the product from a) in 57 ml of acetic acid is treated with 38 ml of 62% aqueous hydrobromic acid. The mixture is boiled under reflux for a total of 3.5 days, subsequently concentrated and the residue is taken up in ethyl acetate, washed with sodium hydrogen carbonate solution and saturated sodium chloride solution. The organic phase is dried and concentrated. There are obtained 1.2 g of 4-(4-bromo-phenyl)-1H-benzo[d][1,2]oxazin-7-ol, MS: m/e 302 (M−H$^-$, 1 Br).

c) A mixture of 1.28 g of 4-(4-bromo-phenyl)-1H-benzo[d][1,2]oxazin-7-ol, 2.71 g of (E)-1,4-dibromo-2-butene and 1.74 g of potassium carbonate in 80 ml of acetone is stirred at 65° C. After cooling the reaction mixture is filtered and the filtrate is concentrated and purified by chromatography (silica gel, toluene/acetone 98:2). There are obtained 1.44 g of 7-(4-bromo-but-2-enyloxy)-4-(4-bromo-phenyl)-1H-benzo[d][1,2]oxazine, MS: m/e 437 (64%, M$^+$, 2 Br).

d) 1.35 g of 7-(4-bromo-but-2-enyloxy)-4-(4-bromo-phenyl)-1H-benzo[d][1,2]oxazine are dissolved in 50 ml of acetone and treated with 3.83 ml of N-allyl-methyl-amine and 1.28 g of potassium carbonate. The mixture is stirred and subsequently filtered. After concentration the filtrate is chromatographed over silica gel with toluene/acetone/triethylamine (92:7:1). There are obtained 1.09 g of (E)-allyl-[4-[4-(4-bromo-phenyl)-1H-benzo[d][1,2]oxazin-7-yloxy]-but-2-enyl]-methyl-amine which is converted into the fumarate, MS: m/e 427 (M+H$^+$, 1 Br).

EXAMPLE 28

Analogously to Example 27:

a) From 4-(4-bromo-phenyl)-1H-benzo[d][1,2]oxazin-7-ol and 1,6-dibromohexane there is obtained 7-(6-bromo-hexyloxy)-4-(4-bromo-phenyl)-1H-benzo[d][1,2]oxazine and by reaction with N-allyl-methyl-amine there is obtained allyl-6-[4-(4-bromo-phenyl)-1H-benzo[d][1,2]oxazin-7-yloxy]-hexyl-methyl-amine which is converted into the fumarate, MS: m/e 457 (M+H$^+$, 1 Br), b) from anisole and 4-bromo-2-methyl-benzoyl chloride there is obtained (4-bromo-2-methyl-phenyl)-(4-methoxy-phenyl)-methanone which, after bromination, addition of tert-butyl N-hydroxy-carbamate, subsequent cyclization and cleavage of the methoxy protecting group, gives 4-(7-bromo-1H-benzo[d][1,2] oxazin4-yl)-phenol, MS: m/e 303 (M$^+$, 1 Br), which is converted with 1,6-dibromohexane into 7-bromo-4-[4-(6-bromo-hexyloxy)-phenyl]-1H-benzo[d][1,2] oxazine and by reaction with N-allyl-methyl-amine into allyl-[6-[4-(7-bromo-1H-benzo[d][1,2]oxazin-4-yl)-phenoxy]-hexyl]-methyl-amine which is converted into the fumarate, MS: m/e 457 (M+H$^+$, 1 Br), c) from 4-(7-bromo-1H-benzo[d][1,2]oxazin-4-yl)-phenol (intermediate in Ex. 28b) and (E)-1,4-dibromobutene there is obtained 7-bromo-4-[4-(4-bromo-but-2-enyloxy)-phenyl]-1H-benzo[d][1,2] oxazine and by reaction with N-allyl-methyl-amine there is obtained (E)-allyl-[4-[4-(7-bromo-1H-benzo[d][1,2]oxazin-4-yl)-phenoxy]-but-2-enyl-methyl-amine which is converted into the fumarate, MS: m/e 427 (M+H$^+$, 1 Br)

EXAMPLE 29 a) A solution of 3 g of (4-bromo-phenyl)-(2-methyl-4-methoxy-phenyl)-methanone (intermediate in Ex. 27a) in 250 ml of tetrachloromethane is treated with 3.9 g of N-bromosuccinimide and a spatula tip of dibenzoyl peroxide. The reaction mixture is irradiated, stirred at room temperature and the separated precipitate is subsequently filtered off. From the filtrate there are isolated after washing with saturated sodium hydrogen carbonate solution and sodium chloride solution and concentration 4.5 g of (4-bromo-phenyl)-(2-dibromomethyl-4-methoxy-phenyl)-methanone, MS: m/e 460 (M$^+$, 2 Br).

b) Cleavage of the methoxy protecting group is effected analogously to Ex. 1b with 50 ml of 1M BBr$_3$ in methylene chloride and gives 4.0 g of (4-bromo-phenyl)-(2-dibromomethyl-4-hydroxyphenyl)-methanone, MS: m/e 446 (M$^+$, 2 Br).

c) This compound is treated with 200 ml of 85% formic acid and heated to 90° C. for 1.5 hrs. After concentration the residue is taken up in methylene chloride and washed with saturated sodium hydrogen carbonate solution as well as sodium chloride solution. The organic phase is dried and concentrated. There are obtained 2.5 g of 2-(4-bromo-benzoyl)-5-hydroxy-benzaldehyde, MS: m/e 304 (M$^+$, 1 Br).

d) Analogously to Example 27c, from 2-(4-bromo-benzoyl)-5-hydroxy-benzaldehyde and 1,6-dibromohexane there is obtained 2-(4-bromo-benzoyl)-5-(6-bromo-hexyloxy)-benzaldehyde and by reaction with N-allyl-methyl-amine there is obtained 5-[6-(allyl-methyl-amino)-hexyloxy]-2-(4-bromo-benzoyl)-benzaldehyde, MS: m/e 458 (M+H$^+$, 1 Br).

e) 0.22 g of the aldehyde from d) is stirred with 0.12 ml of hydrazine hydrate in 10 ml of ethanol at room temperature. Subsequently, the reaction mixture is concentrated and the residue is taken up in methylene chloride, washed with saturated sodium hydrogen carbonate solution and sodium chloride solution, dried over sodium sulphate and concentrated. There is obtained 0.2 g of allyl-[6-[1-(4-bromo-phenyl)-phthalazin-6-yloxy]-hexyl]-methyl-amine which is converted into its fumarate, MS: m/e 454 (M+H$^+$, 1 Br).

EXAMPLE 30

Analogously to Example 29, from 2-(4-bromo-benzoyl)-5-hydroxy-benzaldehyde and (E)-1,4-dibromobutene there is obtained 2-(4-bromo-benzoyl)-5-(4-bromo-but-2-enyloxy)-benzaldehyde and then by reaction with N-allyl-methyl-amine there is obtained 5-[4-(allyl-methyl-amino)-but-2-enyloxy]-2-(4-bromo-benzoyl)-benzaldehyde, MS: m/e 428 (M+H$^+$, 1 Br).

With hydrazine hydrate the latter gives (E)-allyl-[4-[1-(4-bromo-phenyl)-phthalazin-6-yloxy]-but-2-enyl]-methyl-amine which is converted into its fumarate and into its hydrochloride, MS: m/e 424 (M+H$^+$, 1 Br).

EXAMPLE 31

(E)-Allyl-[4-[3-(4-bromo-phenyl)-5-fluoro-1-methyl-1H-indazol-6-yloxy]-but-2-enyl]-methyl-amine A mixture of 0.53 ml of methyl hydrazine and 0.17 g of potassium carbonate is stirred in 5 ml of DMA at room temperature. After the addition of 0.44 g of (E)-[4-[4-(allyl-methyl-amino)-but-2-enyloxy]-2,5-difluoro-phenyl]-(4-bromo-phenyl)-methanone in 5 ml of DMA the mixture is boiled at 120° C. After filtration the filtrate is concentrated at 80° C./0.3 Torr, taken up in methylene chloride, filtered over sodium sulphate and concentrated. The residue consisting of the title compound is dissolved in ether/hexane, treated with 0.11 g of fumaric acid and stirred. After filtration and drying there is obtained 0.41 g of (E)-allyl-[4-[3-(4-bromo-phenyl)-5-fluoro-1-methyl-1H-indazol-6-yloxy]-but-2-enyl]-methyl-amine.fumarate, m.p. 135°–137° C.

0.21 g of the fumarate is converted with methylene chloride/saturated sodium bicarbonate solution into the free base and treated in methylene chloride at 0° C. with 4.8M hydrochloric acid in ether. After evaporation there is obtained 0.15 g of (E)-allyl-[4-[3-(4-bromo-phenyl)-5-fluoro-1-methyl-1H-indazol-6-yloxy]-but-2-enyl]-methyl-amine.hydrochloride, MS: m/e 444 (M+H$^+$, 1 Br).

The starting material (m.p. of the hydrochloride: 150° C.) is obtained from 4-bromobenzoyl chloride and 2,5-difluoroanisole and (E)-1,4-dibromobutene via (4-bromo-phenyl)-(2,5-difluoro-4-methoxy-phenyl)-methanone, (4-brom-phenyl)-(2,5-difluoro-4-hydroxy-phenyl)-methanone and (E)-[4-(4-bromo-but-2-enyloxy)2,5-difluoro-phenyl]-(4-bromo-phenyl)-methanone.

EXAMPLE 32

Analogously to Example 31, a) from [4-[6-(allyl-methyl-amino)-hexyloxy]-2-fluoro-phenyl](4-bromo-phenyl)-methanone there is obtained allyl-[6-[3-(4-bromo-phenyl)-1-methyl-1H-indazol-6-yloxy]-hexyl]-methyl-amine.fumarate (1:1), MS: m/e 456 (M+H$^+$, 1 Br), b) from (E)-[4-[4-(allyl-methyl-amino)-but-2-enyloxy]-3-fluoro-phenyl]-(2,6-difluoro-phenyl)-methanone there is obtained (E)-allyl-[4-[2-fluoro-4-(4-fluoro-1-methyl-1H-indazol-3-yl)-phenoxy]-but-2-enyl]-methyl-amine.fumarate (1:1), m.p. 108°–111° C., c) from (E)-[4-[4-(allyl-methyl-amino)-but-2-enyloxy]-2-fluoro-phenyl]-(4-bromo-phenyl)-methanone there is obtained (E)-allyl-[4-[3-(4-bromo-phenyl)-1-methyl-1H-indazol-6-yloxy]-but-2-enyl]-methyl-amine.fumarate (1:1), m.p. 50°–60° C. (decomposition), MS: m/e 426 (M+H$^+$, 1 Br), d) from [4-[6-(allyl-methyl-amino)-hexyloxy]-phenyl]-(4-bromo-2-fluoro-phenyl)-methanone (Ex. Ad) there is obtained allyl-[6-[4-(6-bromo- 1-methyl-1H-indazol-3-yl)-phenoxy]-hexyl]-methyl-amine.fumarate (1:1), m.p. 152°–154° C. (decomposition), e) from 1-[4-[6-(allyl-methyl-amino)-hexyloxy]-2-fluoro-pheny[-5-methyl-hex-5-en-1-one there is obtained allyl-methyl-[6-[1-methyl-3-(4-methyl-pent-3-enyl)-1H-indazol-6-yloxy]-hexyl]amine.fumarate (1:1), MS: m/e 383 (M), f) from 1-[4-[6-(allyl-methyl-amino)-hexyloxy]-2-fluoro-pheny]ethanone (Ex. Ae) there is obtained allyl-[6-(1,3-dimethyl-1H-indazol-6-yloxy)-hexyl]-methyl-amine.fumarate (1:1), MS: m/e 315 (M), g) from (E)-1-[4-[4-(allyl-methyl-amino)-but-2-enyloxy]-2-fluoro-phenyl]-ethanone there is obtained (E)-allyl-[4-(1,3-dimethyl-1H-indazol-6-yloxy)-but-2-enyl]-methyl-amine, MS: m/e 286 (M+H$^+$), h) from (E)-1-[4-[(E)-4-(allyl-methyl-amino)-but-2-enyloxy]-2-fluoro-phenyl]-5-methyl-4-hexen-1-one there is obtained (E)-allyl-methyl-[4-[1-methyl-3-(4-methyl-pent-3-enyl)-1H-indazol-6-yloxy]-but-2-enyl]-amine.fumarate (1:1), MS: m/e 354 (M+H$^+$), i) from (4-bromo-phenyl)-[4-[6-(cyclopropyl-methyl-amino)-hexyloxy]-2-fluoro-phenyl]-methanone there is obtained [6-[3-(4-bromo-phenyl)-1-methyl-1H-indazol-6-yloxy]-hexyl]-cyclopropyl-methyl-amine.fumarate (1:1), m.p. 141°–143° C., j) from 1-[4-[6-(cyclopropyl-methyl-amino)-hexyloxy]-2-fluoro-phenyl]-5-methyl-hex-4-en-1-one there is obtained cyclopropyl-methyl-[6-[3-(4-methyl-pent-3-enyl)-1H-indazol-6-yloxy]-hexyl]-amine.fumarate (1:1), m.p. 78°–79° C., k) from [4-[6-(allyl-methyl-amino)-hexyloxy]-2-fluoro-phenyl]-(4-bromo-phenyl)-methanone with hydrazine hydrate in DMSO there is obtained allyl-[6-[3-(4-bromo-phenyl)-1H-indazol-6-yloxy]-hexyl]-methyl-amine.fumarate, m.p. 162°–166° C.

Starting materials

From 1-(2-fluoro-4-hydroxy-phenyl)-5-methyl-hex-4-en-1-one, 1,6-dibromohexane and N-allyl-methyl-amine there is obtained 1-[4-[6-(allyl-methyl-amino)-hexyloxy]-2-fluoro-phenyl-5-methyl-hex-5-en-1-one, MS: m/e 375 (M), the starting material for Example 32e).

From 2-fluoro-4-hydroxy-acetophenone, (E)-1,4-dibromo-2-butene and N-allyl-methyl-amine there is obtained (E)-1-[4-[4-(allyl-methyl-amino)-but-2-enyloxy]-2-fluoro-phenyl]-ethanone, MS: m/e 278 (M+H$^+$), the starting material for Example 32g).

From [4-(6-bromo-hexyloxy)-2-fluoro-phenyl]-(4-bromo-phenyl)-methanone and N-methylcyclopropylamine.hydrochloride there is obtained (4-bromo-phenyl)-[4-[6-(cyclopropyl-methyl-amino)-hexyloxy]-2-fluoro-phenyl]-methanone, MS: m/e 447 (M, 1 Br), the starting material for Example 32i).

From 1-(2-fluoro-4-hydroxy-phenyl)-5-methyl-hex-4-en-1-one, 1,6-dibromohexane and cyclopropyl-methylamine.hydrochloride there is obtained 1-[4-[6-(cyclopropyl-methyl-amino)-hexyloxy]-2-fluoro-phenyl]-5-methyl-hex-4-en-1-one, MS: m/e 376 (M+H$^+$), the starting material for Example 32j).

EXAMPLE 33

Allyl-[6-[4-(4-bromo-phenyl)-quinazolin-7-yloxy]-hexyl]-methyl-amine

A solution of 230 mg of [2-amino-4-[6-(allyl-methyl-amino)-hexyloxy]-phenyl]-(4-bromo-phenyl)-methanone in 0.5 ml of formic acid and 2 ml of formamide is boiled at 165° C. for 25 min., then concentrated and converted into the free amine (title compound) with methylene chloride/saturated sodium bicarbonate solution. After purification (silica gel, methylene chloride/methanol 2.5% to 10%) the residue is dissolved in methylene chloride/ether and treated with 23.7 mg of fumaric acid. After stirring and filtration there are obtained 30 mg of allyl-[6-[4-(4-bromo-phenyl)-quinazolin-7-yloxy]-hexyl]-methyl-amine.fumarate (1:1), m.p 90°–95° C., MS: m/e 454 (M+H$^+$, 1 Br).

Starting material 17.55 g of [4-[6-(allyl-methyl-amino)-hexyloxy]-2-fluoro-phenyl]-(4-bromo-phenyl)-methanone are boiled under reflux with 50.7 ml of 4-methoxybenzylamine and 6.5 g of potassium carbonate in 600 ml of toluene for 23 hrs. After filtration, evaporation and purification over silica gel with methylene chloride/methanol (2.5% to 10%) there are obtained 17.43 g of [4-[6-(allyl-methyl-amino)-hexyloxy]-2-[(4-methoxy-benzyl)amino]-phenyl]-(4-bromo-phenyl)-methanone. A solution of this material in 200 ml of trifluoroacetic acid is stirred at room temperature for 45 hrs., evaporated and converted into the free base with methylene chloride/saturated sodium bicarbonate solution. After purification over silica gel with methylene chloride/methanol (9:1) there are obtained 13.23 g of [2-amino-4-[6-(allyl-methyl-amino)-hexyloxy]-phenyl]-(4-bromo-phenyl)-methanone, m.p. of the fumarate 78° C.(decomposition).

EXAMPLE 34

(RS)-Allyl-[6-[4-(4-bromo-phenyl)-3,4-dihydro-quinazolin-7-yloxy]-hexyl]-methyl-amine A solution of 445 mg of [2-amino-4-[6-(allyl-methyl-amino)-hexyloxy]-phenyl]-(4-bromo-phenyl)-methanone in 1 ml of formic acid and 4 ml of formamide is boiled at 160° C. for 35 hrs., then concentrated and converted into the free amine (title compound) with sodium bicarbonate solution saturated with methylene chloride. The residue is dissolved in methylene chloride/ether and treated with 73 mg of fumaric acid. After stirring the mixture is decanted and the residue is triturated with ether and filtered off. There are obtained 30 mg of (RS)-allyl-[6-[4-(4-bromo-phenyl)-3,4-dihydro-quinazolin-7-yloxy]-hexyl]-methyl-amine.fumarate (1:1), m.p 120° C. (decomposition), MS: m/e 456 (M+H$^+$, 1 Br).

EXAMPLE 35

7-[6-(Allyl-methyl-amino)-hexyloxy]-4-(4-bromo-phenyl)-1-methyl-1H-quinazolin-2-one A solution of 0.16 ml of chlorosulphonyl isocyanate in 0.8 ml of methylene chloride is added dropwise at 0° C. to a solution of 0.69 g of [4-[6-(allyl-methyl-amino)-hexyloxy]-2-methylamino-phenyl]-(4-bromo-phenyl)-methanone in 4 ml of methylene chloride. After 3 hrs. at room temperature the mixture is again cooled to 0° C. and 0.8 ml of chlorosulphonyl isocyanate in 0.5 ml of methylene chloride is added dropwise. After 1 hr. at room temperature the mixture is worked-up with saturated sodium bicarbonate solution/methylene chloride and purified over silica gel with methylene chloride/methanol/25% aqueous ammonium hydroxide (95:5:0.5). There is obtained 0.26 g of 7-[6-(allyl-methyl-amino)-hexyloxy]-4-(4-bromo-phenyl)-1-methyl-1H-quinazolin-2-one, MS: m/e 484 (M+H$^+$, 1 Br).

Starting material

A solution of 2.6 g of [4-[6-(allyl-methyl-amino)-hexyloxy]-2-fluoro-phenyl]-(4-bromo-phenyl)-methanone in 115 ml of dimethylacetamide is boiled at 120° C. with 7.2 ml of 8.03M methylamine in ethanol for 3 hrs., concentrated and chromatographed over silica gel with methylene chloride/methanol (2.5%–10%). There is obtained [4-[6-(allyl-methyl-amino)-hexyloxy]-2-methylamino-phenyl]-(4-bromo-phenyl)-methanone, m.p. of the fumarate 72° C.

EXAMPLE 36

Allyl-[6-[4-(4-bromo-phenyl)-2-methyl-quinolin-7-yloxy]-hexyl]-methyl-amine

A solution of 360 mg of [2-amino-4-[6-(allyl-methyl-amino)-hexyloxy]-phenyl]-(4-bromo-phenyl)-methanone in 1.6 ml of acetic acid is treated with 0.01 ml of $H_2SO_4$ and 0.4 ml of acetone and boiled at 95° C. for 21 hrs., with a further 0.4 ml of acetone being added after 6 hrs. At 0° C. the reaction is poured into an ice-cold solution of 1.2 ml of 25% ammonium hydroxide solution in 3.5 ml of water and the mixture is subsequently extracted with methylene chloride. After drying the organic phase is evaporated and the residue is purified over silica gel with methylene chloride/methanol (95:5). The title compound obtained (200 mg) is crystallized with 24.6 mg of fumaric acid from methylene chloride/methanol/ether. There are obtained 56 mg of allyl-[6-[4-(4-bromo-phenyl)-2-methyl-quinolin-7-yloxy]-hexyl]-methyl-amine.fumarate (1:2), m.p. 88°–93° C., MS: m/e 467 ($M+H^+$, 1 Br).

EXAMPLE 37

Allyl-[6-[4-(4-bromo-phenyl)-2H-chromen-7-yloxy]-hexyl]-methyl-amine

A solution of 0.26 g of (RS)-5-[6-(allyl-methyl-amino)-hexyloxy]-2-[1-(4-bromo-phenyl)-1-hydroxy-allyl]-phenol in 50 ml of o-xylene is boiled at 170° C. on a water separator for 2 hrs., evaporated and the residue is purified over silica gel with methylene chloride/methanol 95:5. There is obtained 0.18 g of allyl-[6-[4-(4-bromo-phenyl)-2H-chromen-7-yloxy]-hexyl]-methyl-amine, MS: m/e 456 ($M+H^+$, 1 Br).
Starting material 8.97 g of [4-[6-(allyl-methyl-amino)-hexyloxy]-2-fluoro-phenyl]-(4-bromo-phenyl)-methanone in 450 ml of THF are stirred with 37 ml of 5.4M sodium methanolate in methanol at room temperature for 14 hrs. and under reflux for 1 hr. The solution is evaporated and the residue is taken up in methylene chloride/10% sodium chloride solution. The organic phase is dried, dissolved in ether and stirred overnight with 2.08 g of fumaric acid. There are obtained 8.17 g of [4-[6-(allyl-methyl-amino)-hexyloxy]-2-methoxy-phenyl]-(4-bromo-phenyl)-methanone.fumarate (m.p. 108°–113° C.).

The fumarate obtained is taken up in methylene chloride/saturated sodium bicarbonate solution and the organic phase is dried and concentrated. 3.09 g of the thus-obtained [4-[6-(allyl-methyl-amino)-hexyloxy]-2-methoxy-phenyl]-(4-bromo-phenyl)-methanone are boiled at 90° C. in 13 ml of acetic acid/7.7 ml of 62% aqueous hydrogen bromide solution for 2 hrs. The reaction mixture is concentrated and the residue is converted into the free base with methylene chloride/saturated sodium bicarbonate solution. The residue contains [4-[6-(allyl-methyl-amino)-hexyloxy]-2-hydroxy-phenyl]-(4-bromo-phenyl)-methanone, MS: m/e 446 ($M+H^+$, 1 Br).

1.0 g of [4-[6-(allyl-methyl-amino)-hexyloxy]-2-hydroxy-phenyl]-(4-bromo-phenyl)-methanone in 9 ml of THF/ether (1:1) is added dropwise during 45 min. at 0° C. to 4.8 ml (1.7M in THF) vinylmagnesium chloride solution. The reaction solution is warmed to room temperature overnight, treated with 3 ml of acetic acid/water (1:1) and worked-up with saturated sodium bicarbonate solution/methylene chloride. After drying the organic phase is concentrated and purified over silica gel with methylene chloride/methanol (95:5). There is obtained 0.64 g of (RS)-5-[6-(allyl-methyl-amino)-hexyloxy]-2-[1-(4-bromo-phenyl)-1-hydroxy-allyl]-phenol, MS: m/e 474 ($M+H^+$, 1 Br).

EXAMPLE 38

Allyl-[6-[4-(4-bromo-phenyl)-quinolin-7-yloxy]-hexyl]-methyl-amine

A solution of 0.5 g of (RS)-1-[4-[6-(allyl-methyl-amino)-hexyloxy]-2-amino-phenyl]-1-(4-bromo-phenyl)-prop-2-en-1-ol is added dropwise at 0° C. within 10 min. to a suspension of 0.25 g of pyridinium chlorochromate in methylene chloride. After 1.5 hr. at room temperature water is added, the mixture is adjusted to pH 12 with 2M sodium hydroxide and extracted with methylene chloride. The organic phase is dried, concentrated and the residue is purified over silica gel with methylene chloride/methanol 95:5 as the eluent. 80 mg of the title compound are obtained. 53 mg thereof are dissolved in methylene chloride/ethyl acetate and stirred with 26 mg of fumaric acid. After filtration there is obtained allyl-[6-[4-(4-bromo-phenyl)-quinolin-7-yloxy]-hexyl]-methyl-amine.fumarate (1:3), m.p 70° C., MS: m/e 453 ($M+H^+$, 1 Br).

The starting material, (RS)-1-[4-[6-(allyl-methyl-amino)-hexyloxy]-2-amino-phenyl]-1-(4-bromo-phenyl)-prop-2-en-1-ol, MS: m/e 473 ($M+H^+$, 1 Br), is obtained by reacting vinylmagnesium chloride with [2-amino-4-[6-(allyl-methyl-amino)-hexyloxy]-phenyl]-(4-bromo-phenyl)-methanone.

EXAMPLE 39

(1RS,2RS)-[2-[1-(4-Bromo-phenyl)-isoquinolin-6-yloxymethyl]-cyclopropylmethyl]-cyclopropyl-methyl-amine A solution of 350 mg of triphenylphosphine, 200 mg of 1-(4-bromo-phenyl)-isoquinolin-6-ol (Ex. 23b) and 103.4 mg (1RS,2RS)-[2-[(cyclopropyl-methyl-amino)-methyl]-cyclopropyl]-methanol in 5.4 ml of THF is treated at room temperature within 1 hr. with 0.22 ml of diethyl azodicarboxylate in 0.5 ml of THF. After stirring for 16 hrs. the mixture is concentrated. The residue is dissolved in ether and precipitated with hexane. The mother liquor is concentrated and the residue is purified over silica gel with ethyl acetate as the eluent. The 75 mg of title compound obtained are treated in methylene chloride/methanol with 17.9 mg of fumaric acid and precipitated with ethyl acetate/ether. There are obtained 33 mg of (1RS,2RS)-[2-[1-(4-bromo-phenyl)-isoquinolin-6-yloxymethyl]-cyclopropylmethyl]-cyclopropyl-methyl-amine.fumarate (1:1), MS: m/e 437 ($M+H^+$, 1 Br).
Starting material 13.4 ml of 2M potassium hydroxide in methanol are added to a solution of 5.0 g of diethyl (1RS,2RS)-1,2-cyclopropanedicarboxylate in 9 ml of methanol. After 2.5 hrs. the mixture is acidified with 8% phosphoric acid and extracted with saturated sodium chloride solution/methylene chloride, dried and concentrated to give 5.1 g of monomethyl (1RS,2RS)-1,2-cyclopropanedicarboxylate.

A solution of 9.3 g of monomethyl (1RS,2RS)-1,2-cyclopropanedicarboxylate, 4.0 ml of N-cyclopropylamine and 11.6 g of N(3-dimethylaminopropyl)-N'-ethylcarbodiimide hydrochloride in 210 ml of methylene chloride is treated at 0° C. with 0.7 g of dimethylaminopyridine and subsequently stirred at room temperature for 2 hrs. The reaction solution is worked-up with methylene chloride/10% potassium hydrogen sulphate solution. The organic phase is washed with saturated sodium bicarbonate solution, dried and concentrated to give 10.6 g of methyl (1RS,2RS)-2-cyclopropylcarbamoyl-cyclopropanecarboxylate.

A solution of 4.9 g of methyl (1RS,2RS)-2-cyclopropylcarbamoyl-cyclopropanecarboxylate and 10.8 ml of methyl iodide in 120 ml of 1,2-dimethoxyethane is treated at 0° C. with 1.2 g of 55% sodium hydride and the mixture is stirred at 0° C. for 22 hrs. After the addition of water the mixture is evaporated and the residue is extracted with 10% potassium hydrogen sulphate solution/ether, washed with saturated sodium chloride solution and the organic phase is dried.

The crude methyl (1RS,2RS)-2-(cyclopropyl-methylcarbamoyl)-cyclopropanecarboxylate is dissolved in 9 ml of THF and added dropwise to a boiling suspension of 1.4 g of lithium aluminium hydride in 40 ml of THF. The reaction mixture is boiled for a further 24 hrs., then cooled to 0° C. and treated with 9 ml of water, dried, filtered and concentrated. The oil obtained is dissolved in methylene chloride, dried and concentrated to give 4.2 g of (1RS,2RS)-[2-[(cylcopropyl-methyl-amino)-methyl]-cyclopropyl] methanol, MS: m/e 156 (M+H$^+$).

Pharmaceutically administerable forms of the following composition can be produced in a manner known per se:

EXAMPLE A

Tablets containing 5 mg of allyl-[6-[1-(4-bromo-phenyl)-isoquinolin-6-yloxy]-hexyl]-methyl-amine as the active ingredient

| Composition: | 1 tablet contains: |
|---|---|
| Active ingredient | 5.0 mg |
| Lactose | 148.0 mg |
| Potato starch | 65.0 mg |
| Magnesium stearate | 2.0 mg |
| | 220.0 mg |

EXAMPLE B

Dragées containing 5 mg of allyl-[6-[1-(4-bromo-phenyl)-isoquinolin-6-yloxy]-hexyl]-methyl-amine The tablets of Ex. A are covered according to a known procedure with a coating which consists essentially of sugar and talc. The finished dragées are polished with the aid of beeswax.

| Dragee weight | 300 mg |
|---|---|

EXAMPLE C

Suppositories containing 5 mg of allyl-[6-[1-(4-bromophenyl)-isoquinolin-6-yloxy]-hexyl]-methyl-amine as the active ingredient

| Composition: | 1 suppository contains: |
|---|---|
| Active ingredient | 5.0 mg |
| Suppository mass (e.g. Witepsol W 45 ®) | 1695.0 mg |
| | 1700.0 mg |

EXAMPLE D

Capsules containing 5 mg of allyl-[6-[1-(4-bromo-phenyl)-isoquinolin-6-yloxy]-hexyl]-methyl-amine as the active ingredient

| Composition: | 1 capsule contains: |
|---|---|
| Active ingredient | 5.0 mg |
| Lactose | 82.0 mg |
| Starch | 82.0 mg |
| Magnesium stearate | 1.0 mg |
| | 170.0 mg |

We claim:
1. A compound of the formula:

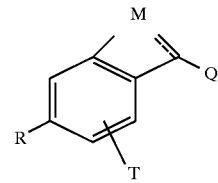

wherein

R is either a group of the formula:

T is H, $C_1$–$C_6$ alkyl, halogen, $N(R^2,R^{21})$, $CONH_2$, CN, $NO_2$, $CF_3$, OH, $C_1$–$C_6$ alkyl(O), or $C_1$–$C_6$ alkyl(S), $R^2$ and $R^{21}$ are independently $C_1$–$C_6$ alkyl or H, and Q is $C_3$–$C_6$ cycloalkyl, phenyl substituted by $R^3$, $C_2$–$C_6$ alkenyl, $C_2$–$C_6$ alkenyl substituted by OH, $C_4$–$C_6$ alkadienyl, or $C_4$–$C_6$ alkadienyl substituted by OH, or wherein one of R and T is halogen or H, and the other of R and T is H, $C_1$–$C_6$ alkyl, halogen, $N(R^2,R^{21})$, $CONH_2$, CN, $NO_2$, $CF_3$, OH, $C_1$–$C_6$ alkyl(O), or $C_1$–$C_6$ alkyl(S), and Q is a group of the formula:

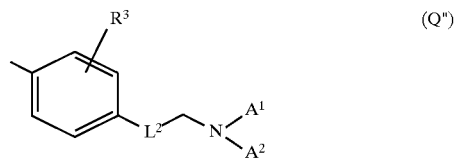

$A^1$ is $C_1$–$C_6$ alkyl or $C_3$–$C_6$ alkenyl, and $A^2$ is $C_3$–$C_6$ cycloalkyl, $C_3$–$C_6$ cycloalkyl-$C_1$–$C_6$-alkyl, $C_1$–$C_6$ alkyl, $C_1$–$C_6$ alkyl substituted by $R^4$, $C_2$–$C_6$ alkenyl, or $C_2$–$C_6$ alkenyl substituted by $R^4$, or $A^1$ and $A^2$ together are a $C_2$–$C_5$ alkylene, a $C_2$–$C_5$ alkylene substituted by $R_4$, $C_4$–$C_5$ alkenylene, or a $C_4$–$C_5$ alkenylene substituted by $R^4$ group $A^1$–$A^2$, $R^4$ is OH, $C_1$–$C_6$ alkyl(O) or $C_1$–$C_6$ alkyl(S) bonded to a saturated C atom of $A^2$ or of $A^1$–$A^2$, whereby a C atom substituted by $R^4$ or an unsaturated C atom present in $A^1$, $A^2$ or $A^1$–$A^2$ is bonded in a position other than the a-position to $N(A^1$–$A^2)$, $L^1$ is a group L bonded to the benzo group directly or via O, NH, $N(C_1$–$C_6$ alkyl), or $N(C_1$–$C_6$ alkanoyl), $L^2$ is a group L bonded to the phenyl group via O, NH, $N(C_1$–$C_6$ alkyl), or $N(C_1$–$C_6$ alkanoyl), L is a $C_4$–$C_{11}$ alkylene, $C_3$–$C_{11}$ alkenylene, or ($C_3$-6-cycloalkylene)-($C_1$–$C_{13}$ alkylene) bonded to the methylene group via its cycloalkylene group, $R^3$ is independently H, $C_1$–$C_6$ alkyl, halogen, $N(R^5,R^{51})$, $CONH_2$, CN, $NO_2$, $CF_3$, OH, $C_1$–$C_6$ alkyl(O), or $C_1$–$C_6$ alkyl(S), $R^5$ and $R^{51}$ are $C_1$–$C_6$ alkyl or H;

----- is a single bond or a double bond:

M is a two-membered grouping having a first member selected from the group consisting of S, SO, and $SO_2$, and a second member selected from the group consisting of N and $N(R^6)$;

$R^6$ is H or $C_1$–$C_6$ alkyl;

and physiologically useful acid addition salts thereof.

2. The compound according to claim 1, of the formula:

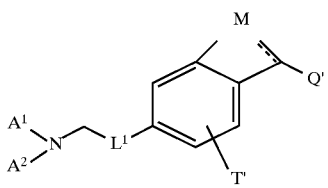

wherein

T' is H, $C_1$–$C_6$ alkyl, halogen, $N(R^2,R^{21})$, $CONH_2$, CN, $NO_2$, $CF_3$, OH, $C_1$–$C_6$ alkyl(O) or $C_1$–$C_{20}$ alkyl(S);

Q' is $C_3$–$C_6$ cycloalkyl, phenyl substituted by $R^3$, $C_2$–$C_6$ alkenyl, $C_2$–$C_6$ alkenyl substituted by OH, $C_4$–$C_6$ alkadienyl, or $C_4$–$C_6$ alkadienyl substituted by OH; and $L^1$ is a group L bonded to the benzo group directly or via O, NH, $N(C_1$–$C_6$ alkyl) or $N(C_1$–$C_6$ alkanoyl).

3. The compound according to claim 1 of the formula:

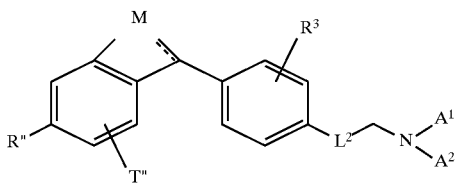

wherein one of R" and T" is halogen or H, and the other one of R" and T" is H, $C_1$–$C_6$ alkyl, halogen, $N(R^2,R^{21})$, $CONH_2$, CN, $NO_2$, $CF_3$, OH, $C1$–$C_6$ alkyl(O), or $C_1$–$C_6$ alkyl(S); and $L^2$ is a group L bonded to the phenyl group via O, NH, or $N(C_1$–$C_6$ alkyl), or $N(C_1$–$C_6$ alkanoyl).

4. The compound according to claim 2 of the formula:

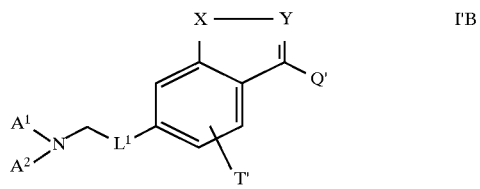

wherein X is S or $SO_2$ and Y is N.

5. The compound according to claim 3 of the formula:

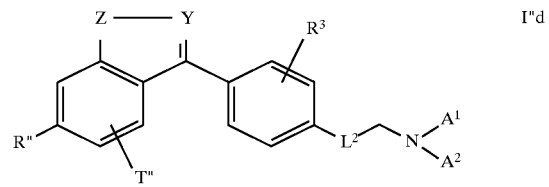

wherein Z is S or $SO_2$.

6. The compound according to claim 4, wherein $A^1$ is $C_1$–$C_6$ alkyl, $A^2$ is $C_2$–$C_6$ alkenyl, $C_3$–$C_6$ cycloalkyl or ($C_1$–$C_4$ alkyl)-S-($C_1$–$C_4$ alkyl), $L^1$ is $C_4$–$C_{11}$ alkylene bonded to the benzo group via an O atom or $C_3$–$C_{11}$ alkenylene group bonded to the benzo group via an O atom, T' is hydrogen or halogen and Q' is phenyl substituted by $R^3$, $C_1$–$C_6$ alkyl, $C_2$–$C_6$ alkenyl, $C_2$–$C_6$ alkenyl substituted by OH, $C_4$–$C_6$ alkadienyl, or $C_4$–$C_6$ alkadienyl substituted by OH.

7. The compound according to claim 5, wherein $A^1$ is $C_1$–$C_6$ alkyl, $A^2$ is $C_2$–$C_6$ alkenyl, $L^2$ is $C_4$–$C_{11}$ alkylene bonded to the phenyl group via an O atom or $C_3$–$C_{11}$ alkenylene bonded to the phenyl group via an O atom, $R^3$ is hydrogen, and R" and T" are hydrogen or halogen.

8. The compound according to claim 4, wherein X—Y is S—N.

9. The compound according to claim 8, wherein $A^1$ is methyl, $A^2$ is allyl, cyclopropyl or methylsulphanylethyl, $L^1$ is n-pentyleneoxy or n-propyleneoxy, Q' is bromophenyl or 4-methyl-pent-3-enyl, and T' is hydrogen or fluorine.

10. The compound of claim 8 which is (E)-allyl-methyl-[4-[3-(4-methyl-pent-3-enyl)-benzo[d]isothiazol-6-yloxy]-but-2-enyl]-amine.

11. The compound of claim 4 which is (E)-Allyl-[4-[3-(4-bromophenyl)-benzo[d]isothiazol-6-yloxy]-but-2-enyl]-methyl-amine.

12. The compound of claim 4 which is (E)-[4-[3-(4-bromo-phenyl)-benzo[d]isothiazol-6-yloxy]but-2-enyl]-methyl-(2-methylsulphanyl-ethyl)-amine.

13. The compound of claim 4 which is allyl-methyl-[6-(3-methyl-benzo[d]isothiazol-6-yloxy)-hexyl]-amine.

14. The compound of claim 4 which is (E)-allyl-methyl-[4-(3-methyl-benzo[d]isothiazol-6-yloxy)-but-2-enyl]-amine.

15. The compound of claim 4 which is allyl-methyl-[6-[3-(4-methyl-pent-3-enyl)-benzo[d]isothiazol-6-yloxy]-hexyl-amine.

16. The compound of claim 4 which is (E)-allyl-methyl-[6-[3-(4-methyl-penta-1,3-dienyl)-benzo[d]isothiazol-6-yloxy]-hexyl]-amine.

17. The compound of claim 4 which is (RS)-1-[6-[6-(allyl-methyl-amino)-hexyloxy]-benzo[d]isothiazol-3-yl]-4-methyl-pent-3-en-2-ol.

18. The compound of claim 4 which is (E)-(RS)-1-[6-[4-(allyl-methyl-amino)-but-2-enyloxy]-benzo[d]isothiazol-3-yl]-4-methyl-pent-3-en-2-ol.

19. The compound of claim 4 which is allyl-methyl-[(E)-4-[3-[(E)-4-methyl-penta-1,3-dienyl]-benzo[d]isothiazol-6-yloxy]-but-2-enyl]-amine.

20. The compound of claim 4 which is 7:3 mixture of (E)-allyl-methyl-[6-[3-(4-methyl-penta-2,4-dienyl)-benzo[d]isothiazol-6-yloxy]-hexyl]-amine and (E)-allyl-methyl-[6-[3-(4-methyl-penta-1,3-dienyl)-benzo[d]isothiazol-6-yloxy]-hexyl]-amine.

21. The compound of claim 4 which is allyl-[6-[3-(4-bromo-1,1-dioxo-benzo[d]isothiazol-6-yloxy]-hexyl)]-methyl-amine.

22. The compound of claim 6 which is allyl-[6-[4-(6-bromo-benzo[d]isothiazol-3-yl)-phenoxy]-hexyl]-methyl-amine.

23. The compound of claim 6 which is (E)-allyl-[4-[4-(6-bromo-benzo[d]isothiazol-3-yl)-phenoxy]-but-2-enyl]-methyl-amine.

24. The compound of claim 6 which is allyl-[6-[4-(6-bromo-1,1-dioxo-benzo[d]isothiazol-3-yl)-phenoxy]-hexyl]-methyl-amine.

25. A compound of the formula:

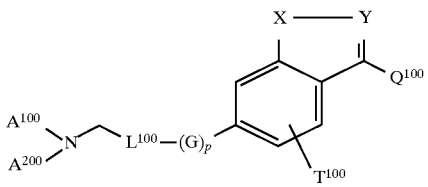

wherein $A^{100}$ is $C_1$–$C_6$ alkyl or $C_3$–$C_6$ alkenyl;

$A^{200}$ is $C_3$–$C_6$ cycloalkyl, $C_3$–$C_6$ cycloalkyl-$C_1$–$C_6$-alkyl, $C_1$–$C_6$ alkyl, $C_1$–$C_6$ alkyl substituted with OH or O($C_1$–$C_6$ alkyl), $C_3$–$C_6$ alkenyl, $C_3$–$C_6$ alkenyl substituted with OH or O($C_1$–$C_6$ alkyl), or $CH_2CH_2SCH_3$;

$L^{100}$ is $C_4$–$C_{11}$ alkylene, $C_3$–$C_{11}$ alkenylene, or ($C_3$–$C_6$ cycloalkylene)-($C_1$–$C_{13}$ alkylene) bonded to the methylene group via its cycloalkyl group;

P is 0 or 1;

G is O, NH, N($C_1$–$C_6$ alkyl) or N($C_1$–$C_6$ alkanoyl);

$T^{100}$ is H, $C_1$–$C_6$ alkyl, halogen, $NH_2$, NH($C_1$–$C_6$ alkyl), N($C_1$–$C_6$ alkyl)$_2$, $CONH_2$, CN, $NO_2$, $CF_3$, OH, $C_1$–$C_6$ alkyl-O, or $C_1$–$C_6$ alkyl-S;

X is S or $SO_2$;

Y is N; and $Q^{100}$ is $C_3$–$C_6$ cycloalkyl, $C_2$–$C_6$ alkenyl, $C_2$–$C_6$ alkenyl substituted with OH, $C_4$–$C_6$ alkadienyl, $C_4$–$C_6$ alkadienyl substituted with OH, or phenyl substituted with at least one substituent selected from the group consisting of H, $C_1$–$C_6$ alkyl, halogen, $NH_2$, NH($C_1$–$C_6$ alkyl), N($C_1$–$C_6$ alkyl)$_2$, $CONH_2$, CN, $NO_2$, $CF_3$, OH, $C_1$–$C_6$ alkyl-O and $C_1$–$C_6$ alkyl-S, or when X is not oxygen, then $Q^{100}$ can be $C_1$–$C_6$ alkyl or $C_1$–$C_6$ alkyl substituted with OH; and physiologically useful acid addition salts thereof.

26. The compound of claim 25, wherein $A^{100}$ is $C_1$–$C_6$ alkyl or $C_3$–$C_6$ alkenyl;

$A^{200}$ is $C_3$–$C_6$ cycloalkyl, $C_3$–$C_6$ cycloalkyl-$C_1$–$C_6$-alkyl, $C_1$–$C_6$ alkyl, or $C_3$–$C_6$ alkenyl;

$L^{100}$ is $C_4$–$C_6$ alkylene, $C_3$–$C_6$ alkenylene, or ($C_3$–$C_6$ cycloalkylene)-($C_1$–$C_6$ alkylene) bonded to the methylene group via its cycloalkyl group;

P is 1;

G is O, NH, N($C_1$–$C_3$ alkyl) or N($C_1$–$C_3$ alkanoyl);

$T^{100}$ is H, $C_1$–$C_3$ alkyl, halogen, $NH_2$, CN, $NO_2$, $CF_3$ or OH;

X is S or $SO_2$;

Y is N; and $Q^{100}$ is $C_2$–$C_6$ alkenyl, $C_2$–$C_6$ alkenyl substituted with OH, $C_4$–$C_6$ alkadienyl, $C_4$–$C_6$ alkadienyl substituted with OH, or phenyl substituted with a substituent selected from the group consisting of H, halogen, $NH_2$, $CONH_2$, CN, $NO_2$, $CF_3$, $C_1$–$C_6$ alkyl-O and $C_1$–$C_6$ alkyl-S.

27. The compound of claim 26, wherein $A^{100}$ is methyl;

$A^{200}$ is allyl, cyclopropyl or methylsulphanyl-ethyl;

$L^{100}$ is $C_4$–$C_6$ alkylene or $C_3$–$C_6$ alkenylene;

P is 1;

G is O;

$T^{100}$ is H or F;

X is S or $SO_2$;

Y is N; and $Q^{100}$ is $C_2$–$C_6$ alkenyl or phenyl substituted with bromine.

28. The compound of claim 27 which is allyl-[6-[3-(4-bromo-phenyl)-benzo[d]isothiazol-6-yloxy]-hexyl]-methyl-amine.

29. The compound of claim 27 which is 6-[3-(4-bromo-phenyl)-benzo[d]isothiazol-6-yloxy]-hexyl]-methyl-(2-methylsulphanyl-ethyl)-amine.

30. The compound of claim 27 which is (E)-allyl-methyl-[4-[3-(4-methyl-pent-3-enyl)-benzo[d]isothiazol-6-yloxy]-but-2-enyl]-amine.

* * * * *